US010221427B2

(12) United States Patent
Doohan et al.

(10) Patent No.: US 10,221,427 B2
(45) Date of Patent: Mar. 5, 2019

(54) GENE CAPABLE OF ENHANCING SALICYLIC ACID-INDUCED CELL DEATH IN A PLANT CELL AND CONTRIBUTING TO RESISTANCE TO THE FUNGAL VIRULENCE FACTOR DEOXYNIVALENOL, RESISTANCE TO FUSARIUM FUNGI AND FUSARIUM HEAD BLIGHT DISEASE, AND A RECOMBINANT CONSTRUCT INCLUDING THE GENE

(71) Applicant: University College Dublin, National University of Ireland, Dublin, Dublin (IE)

(72) Inventors: Fiona Doohan, Co. Donegal (IE); Guillaume Erard, Tokyo (JP); Alexandre Perochon, Angoulerme (FR); Khairul Ansari, Assam (IN); Arunachalam Chanemougasoundharam, Puducherry (IN); Joanna Kacprzyk, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 0 days.

(21) Appl. No.: 15/325,948

(22) PCT Filed: Jul. 15, 2015

(86) PCT No.: PCT/EP2015/066197
§ 371 (c)(1),
(2) Date: Jan. 12, 2017

(87) PCT Pub. No.: WO2016/008942
PCT Pub. Date: Jan. 21, 2016

(65) Prior Publication Data
US 2018/0016594 A1    Jan. 18, 2018

(30) Foreign Application Priority Data

Jul. 15, 2014  (EP) .................................... 14177179

(51) Int. Cl.
*C12N 15/82*  (2006.01)
*C07K 14/415*  (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

2007/0044171 A1    2/2007  Kovalic et al.

OTHER PUBLICATIONS

Ansari et al "Light Influences How the Fungal Toxin Deoxynivalenol Affects Plant Cell Death and Defense Responses" Toxins vol. 6, pp. 679-692, 2014.
Arunachalam et al "Trichothecene Toxicity in Eukaryotes: Cellular and Molecular Mechanisms in Plants and Animals" Toxicology Letters vol. 217, pp. 149-158, 2013.
Erard et al "Characterisation of a Novel Trichothecene-Responsive Wheat Gene" Phytopathology vol. 97, p. S33, 2007.
Anderson et al "Wheat Fusarium Graminearum Infected Spike cDNA Library Triticum Aestivum cDNA Clone WHE3858_B11_D22, mRNA Sequence" CN009393, 2004.

*Primary Examiner* — Brent T Page
(74) *Attorney, Agent, or Firm* — Cesari and McKenna, LLP

(57) ABSTRACT

The Applicant has identified a novel DON-responsive orphan gene (ENST1—SEQ ID NO: 1), and its promoter, which features DON-responsive elements, which can be used to drive the expression of FHB resistance genes. The Applicant has isolated two variants of the gene from wheat that share approximately 94% homology with ENST1. The Applicant has shown that this gene has homologs of >62% nucleotide sequence identity exist in *Aegilops tauschii, Brachypodium distachyon, Festuca pratensis, Hordeum vulgare* and *Triticum aestivum*.

9 Claims, 6 Drawing Sheets

Specification includes a Sequence Listing.

GENE CAPABLE OF ENHANCING SALICYLIC ACID-INDUCED CELL DEATH IN A PLANT CELL AND CONTRIBUTING TO RESISTANCE TO THE FUNGAL VIRULENCE FACTOR DEOXYNIVALENOL, RESISTANCE TO FUSARIUM FUNGI AND FUSARIUM HEAD BLIGHT DISEASE, AND A RECOMBINANT CONSTRUCT INCLUDING THE GENE

CROSS REFERENCE TO RELATED APPLICATIONS

This application is the National Stage of International Application No. PCT/EP2015/066197, filed on Jul. 15, 2015, which claims the benefit of European Application No. 14177179.0, filed on Jul. 15, 2014. The contents of both applications are hereby incorporated by reference in their entirety.

BACKGROUND TO THE INVENTION

The invention relates to a gene capable of enhancing salicylic acid-induced cell death in a plant cell and contributing to resistance to the fungal virulence factor deoxynivalenol, resistance to *Fusarium* fungi and *Fusarium* head blight disease, and a recombinant construct including the gene. The invention also relates to plant cells transformed with the gene, and plant material including plant cell cultures, seeds, and plants comprising the transformed plant cells.

The phenolic compound salicylic acid is a key signaling molecule for plant disease resistance. Salicylic acid accumulation is induced by pathogen attacks and other stress conditions (Delaney et al. 1994). Exogenous application of salicylic acid or its analogs such as benzo (1,2,3) thiadiazole-7-carothioic acid induces disease resistance in plants (White 1979; Gorlach et al. 1996; Lawton et al. 1996). Salicylic acid postively regulates cell death (Vlot et al. 2009) and in doing so it inhibits the spread of biotrophic pathogens. It is an important component of the defence response to biotrophs and hemibiotrophs such as *F. graminearum* (Makandar et al. 2012). *F. graminearum* is the causal agent of the economically devastating *Fusarium* head blight (FHB) disease of cereals; this pathogen is hemibiotrophic, with a short biotrophic phase preceding a necrotrophic phase (where they feed off dead plant tissue). This disease is important because it causes both yield loss and toxin contamination of small grain cereals such as wheat and barley. Enhancing resistance to the toxin deoxynivalenol (DON) is known to improve resistance to disease. Given the economic importance of FHB, several control strategies have been developed to prevent FHB epidemics. However, the use of host resistance is considered to be the most effective means to control FHB and trichothecene accumulation in wheat. DON is phytotoxic and resistance to DON enhances resistance to *Fusarium* and FHB disease. US2007/0044171 discloses thousands of recombinant polynucleotides that are described as being useful for improvement of plants.

It is the object of the invention to discover novel genes that enhance salicylic acid-induced immunity and contribute to resistance to DON and FHB.

STATEMENTS OF INVENTION

Figure 1:
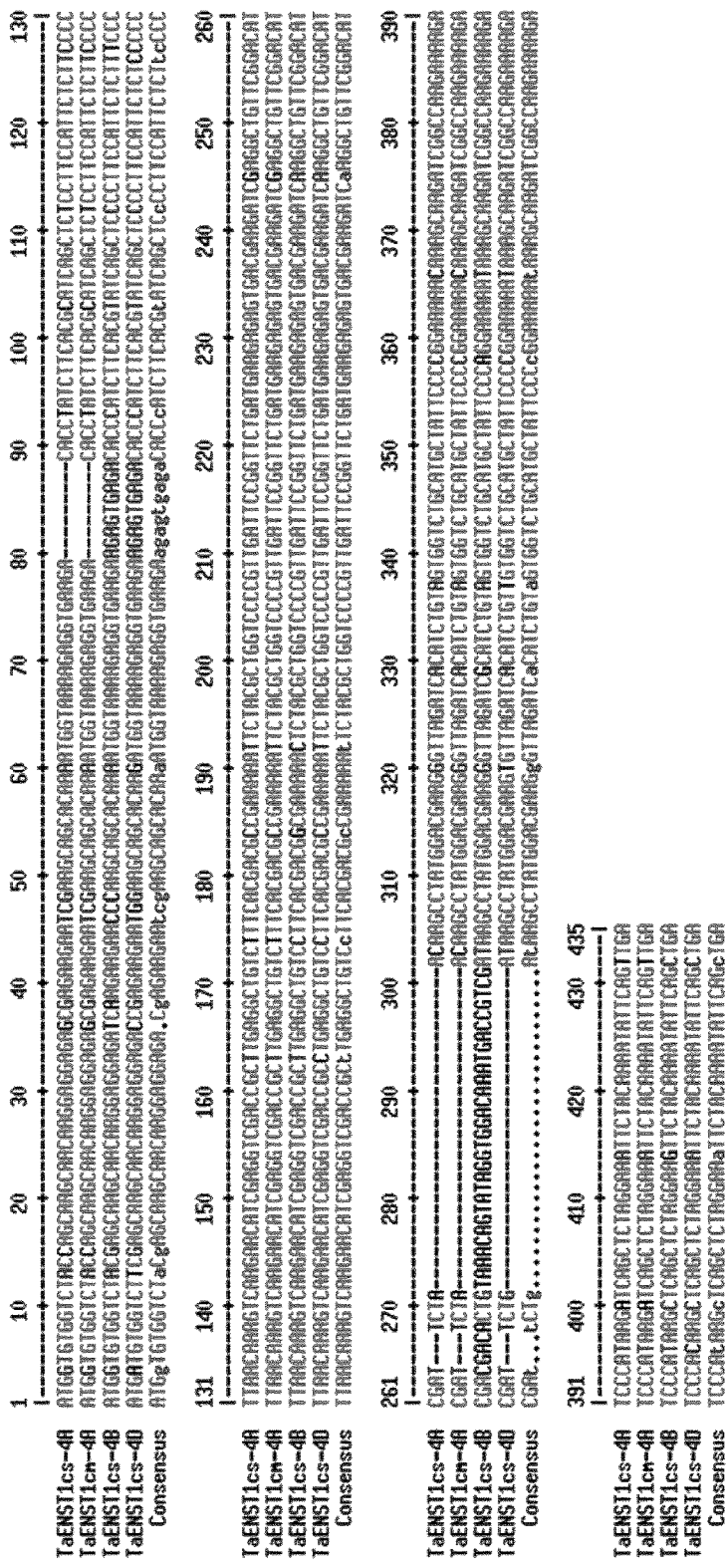
Figure 2:
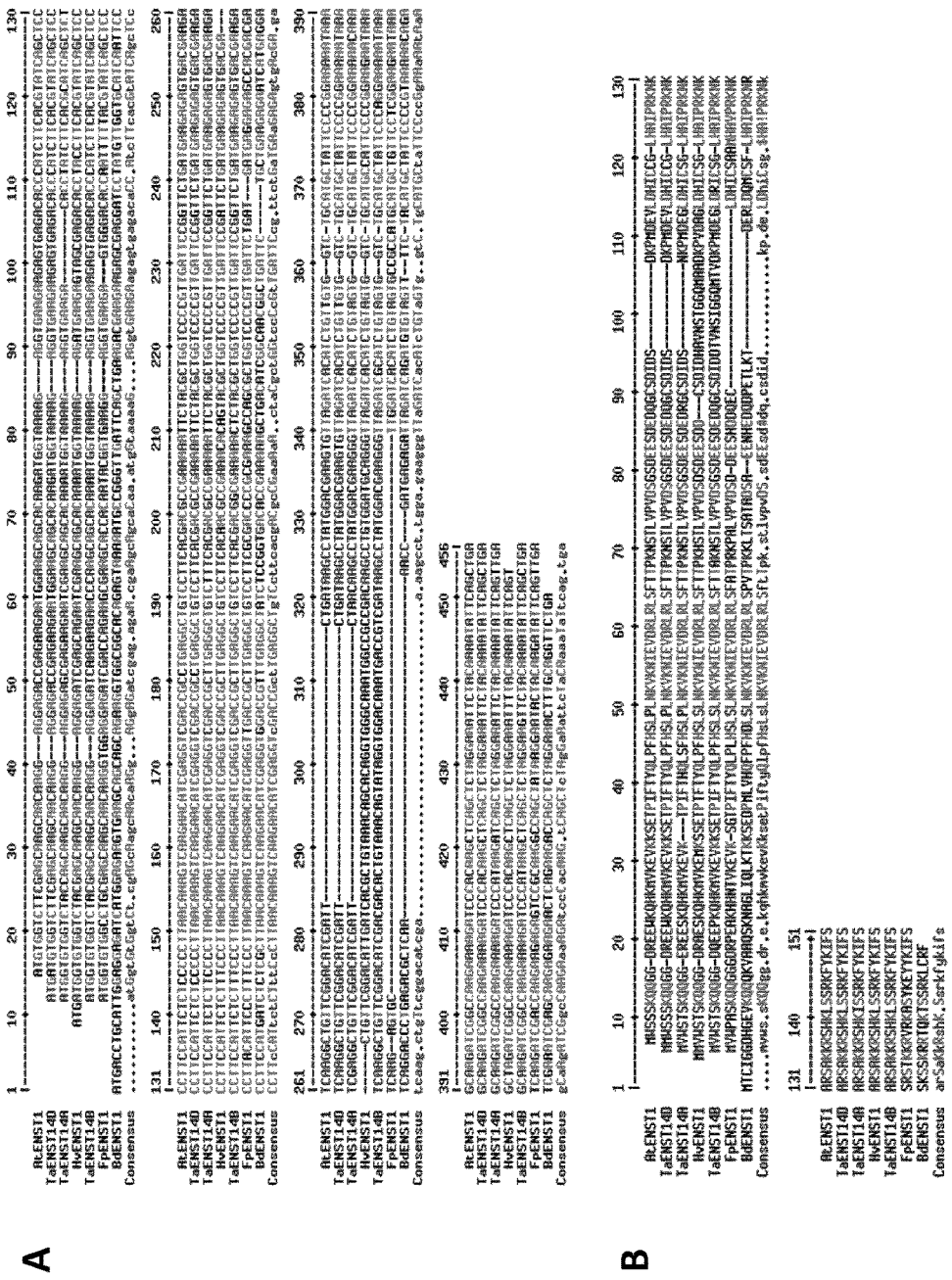
Figure 4:
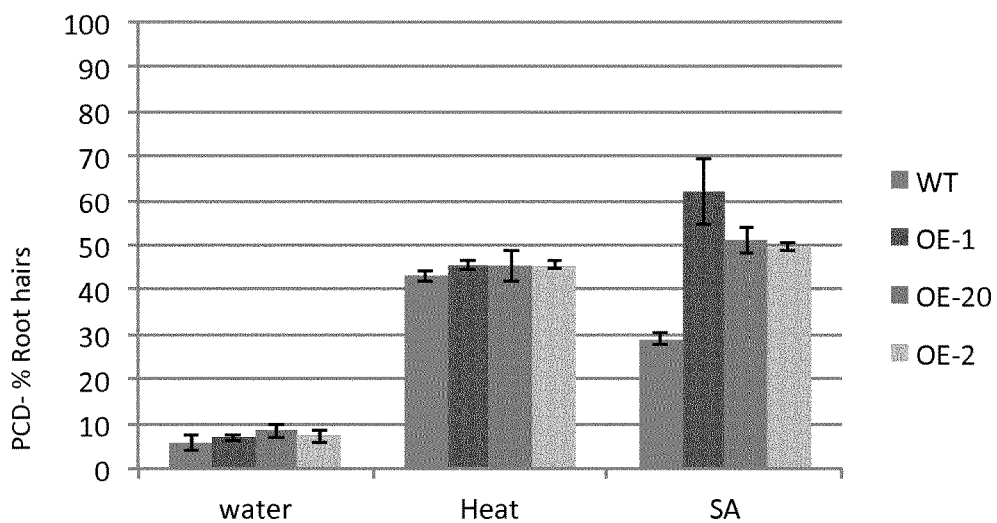
Figure 5:
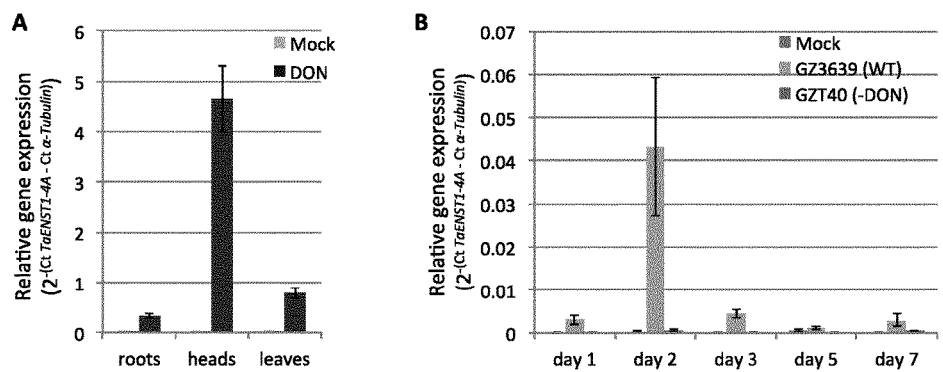
Figure 6:
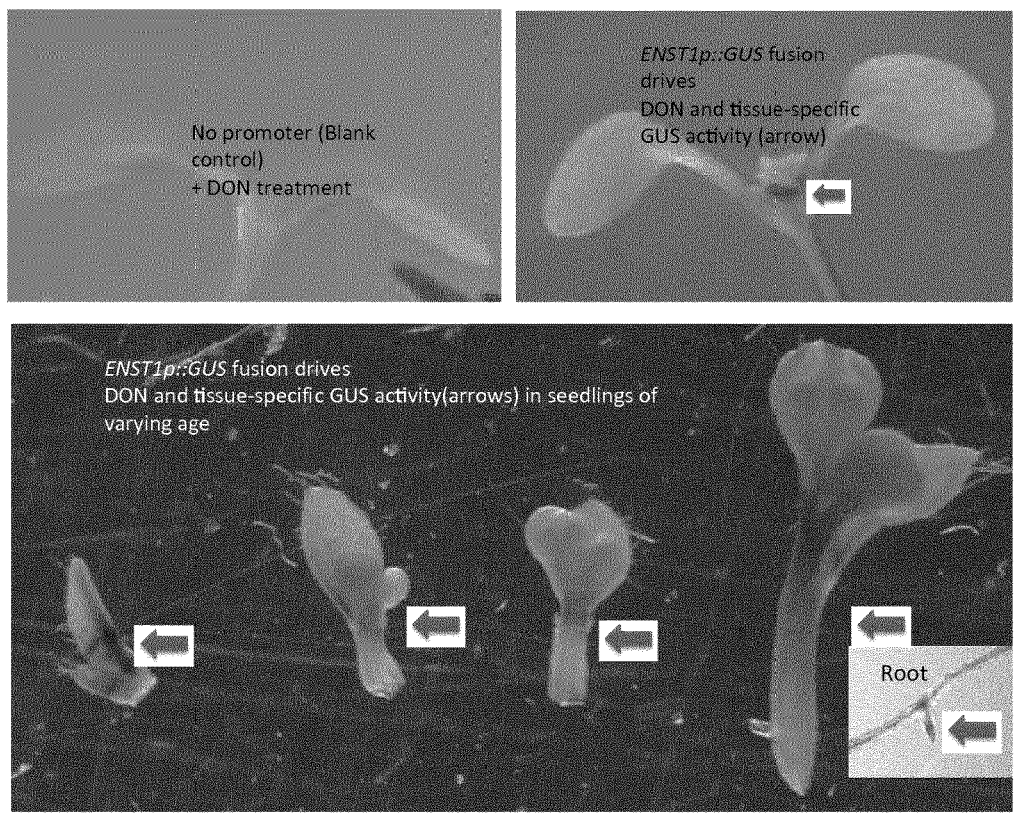
Figure 7:
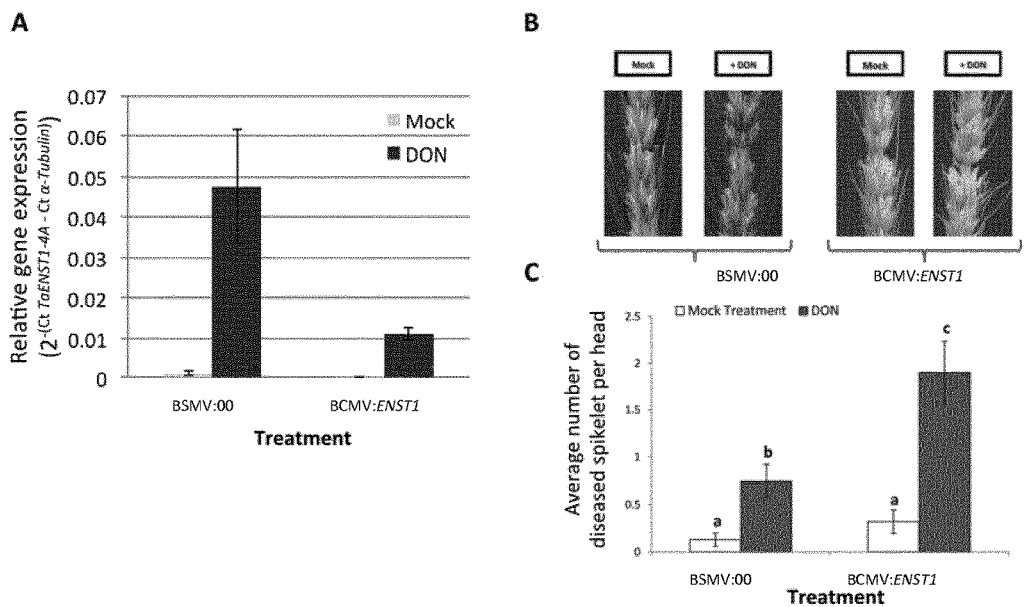

The Applicant has identified a novel DON-responsive orphan gene (ENST1—SEQ ID NO: 1), and its promoter, which features DON-responsive elements, which can be used to drive the expression of FHB resistance genes. A synonym for the gene is FROG (*Fusarium* resistance orphan gene). The Applicant has isolated two variants of the gene (FIG. 1—SEQ ID NO's: 26 and 27) from wheat that share approximately 94% homology with ENST1. The Applicant has shown that this gene has homologs of >62% nucleotide sequence identity that exist in *Aegilops tauschii, Brachypodium distachyon, Festuca pratensis, Hordeum vulgare* and *Triticum aestivum* (FIG. 2). The Applicant has shown that overexpression of ENST1 in three transgenic wheat lines (a) enhanced wheat resistance to colonisation by *F. graminearum* (FIG. 8) and (b) retards the spread of FHB disease symptoms (FIG. 9). The Applicant has shown that overexpression of ENST1 in *Arabidopsis* plants enhanced salicylic acid induced cell death (FIG. 4), an important component of resistance to biotrophic pathogens, and thus has utility for disease-resistant breeding. Furthermore, this gene is responsive to DON and DON-producing *Fusarium* and the promoter, which shares 42% identity with the promoter of the *Brachypodium distachyon* ENST1 homolog, has been cloned and sequenced and has utility for the control of DON-responsive genes (FIGS. 5 & 6). The Applicant has shown that virus-induced gene silencing of ENST1 in wheat heads of cv. CM82036 significantly increased the number of DON-bleached spikelets, as compared to non-silenced control plants (FIG. 7).

The invention provides an isolated polynucleotide comprising SEQUENCE ID NO: 1, or a functional variant thereof having at least 60% sequence identity with SEQUENCE ID NO: 1 (hereafter "polynucleotide of the invention").

The invention also provides an isolated protein encoded by the isolated polynucleotide of the invention (hereafter "protein of the invention").

The invention also provides a recombinant construct comprising a promoter region functional in a plant cell operably linked to a transgene, wherein the transgene comprises a polynucleotide of the invention. Preferably, the promoter region comprises a DON-responsive promoter, and preferably a sequence of SEQUENCE ID NO: 2, or a functional variant thereof having at least 40% sequence identity with SEQUENCE ID NO: 2.

The invention also provides a transformation platform comprising a recombinant construct of the invention. Preferably, the promoter region comprises a DON-responsive promotor. Preferably, the promotor region comprises a sequence of SEQUENCE ID NO: 2. Preferably, the transgene comprises a recombinant polynucleotide of SEQUENCE ID NO: 1. Most preferably, the promoter region comprises a sequence of SEQUENCE ID NO: 2 and the transgene comprises a recombinant polynucleotide of SEQUENCE ID NO: 1.

Typically, the transformation platform comprises a bacteria capable of mediating cellular transformation or biolistic transformation.

The invention also provides plant material genetically transformed with a polynucleotide, recombinant construct or transformation platform of the invention. Typically, the plant material is selected from a plant cell, plant cell culture, plant tissue, plant, or seed for a plant. Typically, the transformed plant material comprises a transformed cell capable of overexpression of a polynucleotide of the invention.

The invention also provides a plant material comprising a plant cell carrying a transgene, in which the transgene comprises the polynucleotide of the invention.

The invention also provides a method of genetically transforming a plant material comprising the steps transforming a cell or cells of the plant material with a polynucleotide, recombinant construct or transformation platform of the invention, wherein the transformed cell or cells is typically capable of overexpression of a polynucleotide of the invention. Typically, the plant material is selected from a plant cell, plant cell culture, plant tissue, plant, or seed for a plant.

The invention also provides a method of producing a transgenic cell which comprises the steps of inoculating cells with a transformation platform comprising a recombinant construct of the invention, culturing the cells under conditions that enable the transformation platform to transform the cells, selectively screening the inoculated cells for transformed cells, and typically isolating the or each transformed cell. Preferably, the recombinant construct comprises a DON-responsive promoter. Most preferably, the recombinant construct comprises a promoter region comprises a promoter region comprising a sequence of SEQUENCE ID NO: 2 and a transgene comprising a recombinant polynucleotide of SEQUENCE ID NO: 1.

The invention also provides a method of producing a transgenic plant comprising the steps of producing a transgenic cell according to a method of the invention, and generating a transformed plant from the transformed cell.

The invention also provides a method of producing a plant having improved property, the method comprising the steps of transforming a plant with a transformation platform according to the invention, or a transformation platform comprising a recombinant construct of the invention, and growing the plant. Preferably, the recombinant construct comprises a DON-responsive promoter. Most preferably, the recombinant construct comprises a promoter region comprises a promoter region comprising a sequence of SEQUENCE ID NO: 2 and a transgene comprising a recombinant polynucleotide of SEQUENCE ID NO: 1. Typically, the improved property is selected from: resistance to FHB disease; resistance to DON; improved yield; improved seed number; improved seed weight; improved resistance to disease.

Preferably, the plant is a cereal plant, preferably a small grain cereal plant. Ideally, the plant is selected from wheat, barley, oats, maize or an *Arabidopsis* plant.

The invention also provides plant material genetically transformed according to a method of the invention, in which at least one cell of the plant material overexpresses a recombinant polynucleotide of the invention. Typically, the plant material is selected from a plant cell, plant cell culture, plant tissue, plant, or seed for a plant.

The invention also relates to a bacteria capable of mediating cellular transformation, and containing a transformation platform according to the invention.

The invention also relates to a seed, transgenic cell, plant cell culture or plant cell, transgenic plant tissue, transgenic plant material, or stable transgenic plant, generated according to a method of the invention.

The invention also relates to a seed, transgenic cell, plant cell culture or plant cell, transgenic plant tissue, transgenic plant material, or stable transgenic plant, containing a transformation platform, or recombinant construct, or recombinant polynucleotide, of the invention.

The invention also relates to a kit of parts capable of genetically transforming a cell, ideally a plant cell, comprising (a) a bacteria capable of mediating cellular transformation, (b) a recombinant construct, and (c) a transgene. The transgene may be located on the unitary transformation vector or may be on a different vector.

The invention also provides an isolated polynucleotide comprising a sequence of SEQUENCE ID NO: 2 or a functional variant thereof having at least 40% sequence identity with SEQUENCE ID NO: 2.

BRIEF DESCRIPTION OF THE FIGURES

FIG. 1. Multiple alignments of ENST1 wheat variants. The coding sequences from wheat variants TaENST1cm-4A (SEQ ID NO: 29) and TaENST1cm-4B (cultivar CM82036) were isolated from a cDNA bank and used to retrieve the different variants from the analyses of the reference wheat genome (cultivar Chinese spring). Resulting sequences TaENST1cs-4A (SEQ ID NO: 26), TaENST1cs-4B (SEQ ID NO: 27), and TaENST1cs-4D (SEQ ID NO: 28) were aligned and compared with those coming from the CM82036 cultivar using MULTALIN. A Consensus sequence (SEQ ID NO: 30) is shown below the alignment.

FIG. 2. Multiple alignments of the different ENST1 homolog. Alignments of the coding sequences (A) or corresponding protein sequences (B) of ENST1 homologs. Sequences were identified by BLASTn analyses against NCBI nucleotide collection, barley (cultivar Morex) and *Brachypodium distachyon* genome. Abbreviations: *Aegilops tauschii* (At), *Brachypodium distachyon* (Bd), *Festuca pratensis* (Fp), *Hordeum vulgare* (Hv) and *Triticum aestivum* (Ta). The coding sequences (A) are shown as AtENST1 (SEQ ID NO: 31), TaENST1 4D (SEQ ID NO: 28), TaENST1 4A (SEQ ID NO: 26), HvENST1 (SEQ ID NO: 32), TaENST1 4B (SEQ ID NO: 27), FpENST1 (SEQ ID NO: 33), BdENST1 (SEQ ID NO: 34), and Consensus (SEQ ID NO: 35). The corresponding amino acid sequences (B) are shown as AtENST1 (SEQ ID NO: 36), TaENST1 4D (SEQ ID NO: 37), TaENST1 4A (SEQ ID NO: 38), HvENST1 (SEQ ID NO: 39), TaENST1 4B (SEQ ID NO: 40), FpENST1 (SEQ ID NO: 41), BdENST1 (SEQ ID NO: 42), and Consensus (SEQ ID NO: 43).

FIG. 3. Molecular characterisation of transgenic lines overexpressing ENST1 in *Arabidopsis thaliana*. The coding sequence of ENST1 was introduced in the binary gateway vector pAM-PAT-GWY under the control of the constitutive double 35S promoter, afterwards this construction was used to transform *Arabidopsis thaliana* by floral dipping. (A) Verification by PCR of the insertion of the T-DNA construction carrying ENST1 in the different *Arabidopsis* transgenic lines (OE-1, OE-2, OE-20) with primers matching with the 35S promoter and the terminator of the T-DNA construction. The wild type plant (Col-0) and the vector utilised for the transformation were used as a PCR positive or negative control respectively. (B) Gene expression of ENST1 in the different transgenic lines as compared to the wild type plant (Col-0) in normal plant growth conditions was determined by RT-PCR analyses.

FIG. 4. Effect of ENST1 over-expression in *Arabidopsis* on the programmed cell death induced by salicylic acid. Wild type plants Col-0 (WT) and three independent lines overexpressing TaENST1-4A (OE-1, OE-2 and OE-20) were tested for their responses to the Salicylic acid (SA). Seedlings were treated with 65 μM SA or at 49° C. (10 min). 24 hours after the treatment a root hair assay was performed assessing the percentage of root hair showing retraction and condensation of the cytoplasm and no FDA staining deemed to have undergone apoptosis-like programmed cell death (AL-PCD). Presented values are means (n=3)±SEM. The experiment was repeated three times.

FIG. 5. Effect of (A) deoxynivalenol (DON) and (B) *Fusarium graminearum* on the transcription of ENST1. (A) Seedling roots, leaves and flowering heads of wheat cv. CM82036 were treated with either DON or Tween-20 (Mock treatment). The tissues were harvested 24 h post-treatment and used for analysis. (B) Wheat heads were treated with either wild type *F. graminearum* GZ3639, its DON-minus mutant derivative GZT40 or Tween-20. The tissues were harvested after different time point post-inoculation as indicated. Data represent TaENST1-4A expression relative to the reference genes α-tubulin using the $2^{-\Delta Ct}$ method following real-time PCR analysis. Results are the average of three (A) or two (B) biological replicates and error bars indicate SEM.

FIG. 6. The promoter region of ENST1 drives beta-D-glucuronidase activity, as demonstrated in *Arabidopsis thaliana*. T2 seedlings were confirmed to be homozygous transformants by kanamycin selection and PCR-based amplification of the promoter region. Seedlings were incubated in DON or mock treatment and stained for GUS activity, and as shown, the promoter drives DON and tissue-specific GUS activity.

FIG. 7. Virus-induced gene silencing (VIGS) of ENST1 in wheat spikelets. Plants of wheat cultivar CM82036 were subjected to virus-induced gene silencing using barley stripe mosaic virus (BSMV) constructs either BSMV:00 (empty vector) or BSMV:ENST1 (construct targeting TaENST1-4A). Flag leaves were treated with the tripartite BSMV plasmids, prior to emergence of the first head, and subsequently inoculated with either DON or Tween-20 (Mock treatment) at mid-anthesis. Data presented are the results obtained for 14 days post inoculation (dpi). (A) Gene silencing in wheat spikelets was quantified by real-time PCR analysis, TaENST1-4A expression is calculated relative to the reference genes α-Tubulin using the $2^{-\Delta Ct}$ method. (B) Images display typical disease symptoms. (C) Quantification of the number of diseased spikelet per head. Results (A) and (C) are the average of two biological replicates with around 16 heads per treatment per constructs. Error bars indicate SEM. Statistically-significant differences were identified using the Kruskal-Wallis test. Columns having different letters are significantly different (P<0.05).

Figure 8:
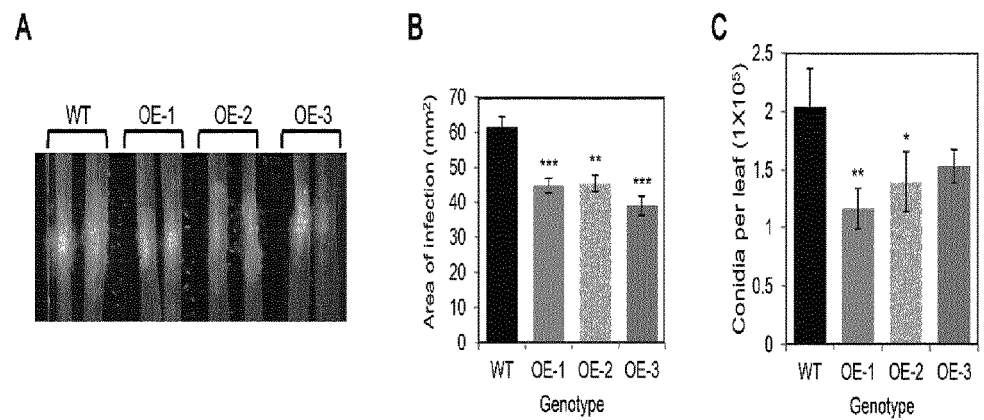
Figure 9:
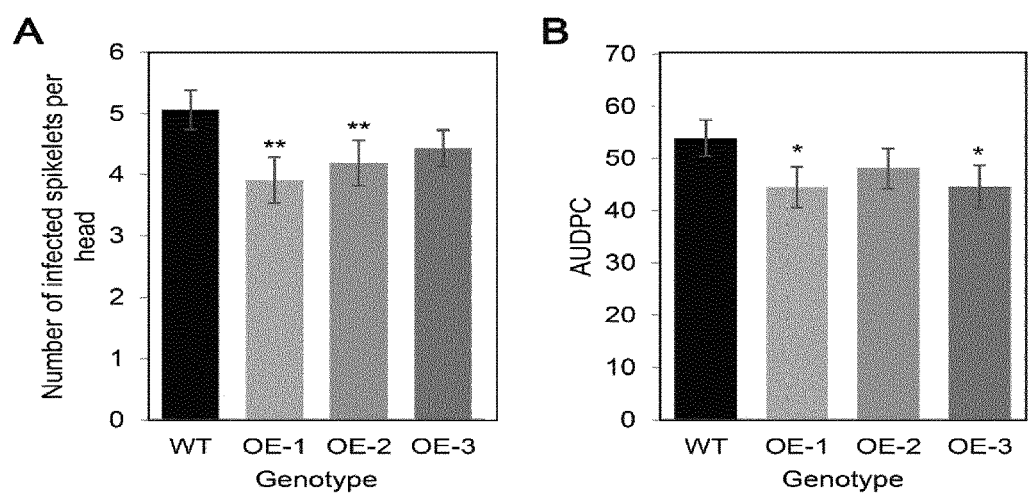

FIG. 8. Effect of TaENST overexpression on wheat leaf resistance to *F. graminearum*. A, B and C, TaENST overexpressor lines (OE-1, OE-2 and OE-3) and control plants (WT) were used for phenotypic analysis. A, Representative leaf symptoms, B, diseased leaf area and C, conidia production were determined 4 days post-treatment of detached wheat leaves with *F. graminearum* plus DON (75 µM). Error bars indicate ±SEM. Asterisks show significant differences compared to the WT ((B) Tukey's HSD test; (C) Mann-Whitney U test; *, P<0.05; , P<0.01; *, P<0.001).

FIG. 9. Effect of TaENST overexpression on the susceptibility of wheat to FHB disease. A and B, At mid-anthesis, central flowering spikelets from overexpressor lines (OE-1, OE-2 and OE-3) or control plants (WT) were point-inoculated with *F. graminearum*. Disease was assessed at 7, 14 and 21 days post inoculation and data presented correspond to the score at (A) 21 days or (B) to the AUDPC. Error bars indicate ±SEM. Asterisks show significant differences compared to the WT (Mann-Whitney U test; *, P<0.05; **, P<0.01).

DETAILED DESCRIPTION OF THE INVENTION

The invention relates to a DON-responsive orphan gene restricted to the Pooideae subfamily of grasses, ENST1, that is capable of enhancing salicylic acid-induced programmed cell death, resistance to the *Fusarium* head blight (FHB) disease virulence factor DON, resistance to *Fusarium* fungi and *Fusarium* head blight disease. The gene is termed ENST1 (a synonym for the gene is FROG—*Fusarium* Resistance Orphan Gene), and the gene sequence is provided below.

[SEQUENCE ID NO: 1]
ATGGTGTGGTCTACCAGCAAGCAACAAGGAGGAGAGCGAGAAGAATCGAA

GCAGCACAAAATGGTAAAAGAGGTGAAGACACCTATCTTCACGCATCAGC

TCTCCTTCCATTCTCTTCCCCTTAACAAAGTCAAGAACATCGAGGTCGAC

CGCTTGAGGCTGTCTTTCACGACGCCGAAAAATTCTACGCTGGTCCCCGT

TGATTCCGGTTCTGATGAAGAGAGTGACGAAGATCGAGGCTGTTCGGACA

TCGATTCTAACAAGCCTATGGACGAAGGGTTAGATCACATCTGTAGTGGT

CTGCATGCTATTCCCCGGAAAAACAAAGCAAGATCGGCCAAGAAAAGATC

CCATAAGATCAGCTCTAGGAAATTCTACAAAATATTCAGTTGA.

The gene encodes a nuclear protein, ENST1, and has been characterised as a nuclear protein that interacts with the stress regulator SNRK1a and a novel NAC transcription factor, as determined by yeast-two hybrid analysis. The sequence of ENST1 is provided below.

[SEQUENCE ID NO: 3]
MVWSTSKQQGGEREESKQHKMVKEVKTPIFTHQLSFHSLPLNKVKNIEVD

RLRLSFTTPKNSTLVPVDSGSDEESDEDRGCSDIDSNKPMDEGLDHICSG

LHAIPRKNKARSAKKRSHKISSRKFYKIFS

The Applicant has also discovered a DON-responsive promoter that is activated in response to DON treatment, as evidenced by gene expression studies (see FIG. 5) and analysis of GUS activity in transformants of *Arabidopsis* carrying a promotor-GUS fusion (see FIG. 7). The sequence of the promoter is provided below:

[SEQUENCE ID NO: 2]
CTGCCTCTTGCGAGCGGGAAGCCAGTGCCACCGCTCGGCATTTCCCGTAC

ATCCGGATCTAAGCTCACCCGTAGCGCGACAATTAGTGGATAGGAGTTGG

GGCCTCACCGAGAAGCACTGCCCTTCCTGGTCCTCCTACCTGCAAAGAGG

TGAAGATGCGGTCGGCCGCACCGCGGTAGCTCGACGGCTCCGTGAATGGT

GGGGCAGATGCCACGTTGCTGCATGGCTCCGCGCGACTGSCMACATGAAT

GGTGGCGACGGGTACGAAAGTGGCGGCAGCTACAACTTCGCGCCGACATG

AGTATCCCGAGCCTCCTTCGCCGTCTCGTGCACCTTTTTTTAACAAATTA

AGAAGCTTTTTGCCCTTCTGGGATACTGCTGGGCCCGAGGCGGAGTGAAT

CTGGGCGGGTTGGGTACAACCATACAAGGAGGAAGAATGTGGGAGTAGTG

GGGTGGTTGACCTGCTTTTCTTCGGTTCAGTTCGCTCCTGTTCAAAAGAA

TGACCAACTAGGAGAAAAAACCAAAAGCAAAAATAAACTGTCAACGTGGC

AAGCGCTAAAATTGAGAGAAGAAAAACCAAGTTAAAATGTAAACACGAGG

GTAAAATGTGGCACAAAGTGCAAAAGTGAAGGTACTCACCTGCCAAAATG

AAAGTGAAGGTGCTCCCTCCTTCCCAAAATATAAGGCGCGGATTGACTTT

```
-continued
TCTGGTCTTTATTGTGCAACTTTGACTATAATTTTCATGTATTCGTTACA

AGACAAATACGATGATGCCATTTATACATATTCAATCAATATACTTTGAT

ATATATTAATGGTCAAAGTCGTGCATAAAAAACCGCCTTATATTTTAGGA

AAGAGGAAGTATAAATTAAGGATTTTCTCCGGGTTAAATGAAATTAACTC

TTATTTTATTAATGTCCACACCGGAGGCCTCCCCCTTGTTAGAATCCTGA

CTCCATCCCTGATCACGGCTGTCCGGTTGGATGCCCACCAAGGCATTTTT

CCTCTCCCCGTACATGTGCAAATGGATAGCGACCTTGGCAACCAAGAAAA

TGGATATCGACAAGATTCGTCAGACGAGTCAGCGACGAAGAACCTTGGCA

ACCAAGGCGCGCGGCAGCCACCGTGACGATCAAGTCAAATAATCATCTGA

CCTCGTGCTTCCGCTCACATCCGTCGTTTTCGTCCTGGACGAACCTTCAC

GCAGCTTTCTCCCCTCAGCTTCTCTCTCTTCGCCCCTCACAACTTATATA

TAAGTGTCGCACTACTAGATCCTCAAC
```

As used herein, the term "isolated" should be understood to mean isolated from its natural environment or produced by means of a technical process for example recombinant DNA technology.

As used herein, the term "functional variant thereof" as applied to SEQUENCE ID NO: 1 (enst1 gene) should be understood to mean a polynucleotide having at least 60%, 62%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity with SEQUENCE ID NO: 1 and which is typically capable of enhancing salicylic acid-induced cell death when overexpressed in Arabidopsis plants using the methods described below. Thus, the functional variant refers to any second polynucleotide varying from a first polynucleotide sequence in such a way so as not to significantly affect the function when compared to the function of the first polynucleotide, and such functional variants may be naturally occurring, or may be non-natural functional variants. Functional wheat variants of SEQUENCE ID NO: 1 having approximately 94% sequence homology with ENST1 are provided in FIG. 1—TaENST1cs-4A (SEQ ID 26), TaENST1cs-4B (SEQ ID 27) and TaENST1cs-4D (SEQ ID 28).

As used herein, the term "functional variant thereof" as applied to SEQUENCE ID NO: 2 (DON-responsive promoter) should be understood to mean a polynucleotide having at least 40%, 42%, 50%, 60%, 70%, 80%, 81%, 82%, 83%, 84%, 85%, 86%, 87%, 88%, 89%, 90% 91%, 92%, 93%, 94%, 95%, 96%, 97%, 98%, 99% sequence identity with SEQUENCE ID NO: 2, which is DON responsive, and which is capable of promoting overexpression of the ENST1 gene in Arabidopsis plants using the methods described below. Thus, the functional variant refers to any second polynucleotide varying from a first polynucleotide sequence in such a way so as not to significantly affect the function when compared to the function of the first polynucleotide, and such functional variants may be naturally occurring, or may be non-natural functional variants.

In this specification, the term "sequence identity" should be considered to include both sequence identity and similarity, i.e. a gene sequence that shares at least 98% sequence identity with a reference sequence is one in which any 98% of aligned nucleotides at least are either identical to, or conservative substitutions of, the corresponding residues in the reference sequence.

In this specification, the term "plant material" should be understood to mean any constituent of a plant comprising plant cells, including a plant cell, plant cell culture, plant tissue, plant, or seed from a plant. A "transgenic seed" refers to a seed that contains a transgene incorporated, ideally stably incorporated, into its genome.

In this specification, the term "cell" should be understood to mean a cell from a plant or fungus. Typically, the cell is obtained from a monocotyledon or dicotyledon plant. In a particularly preferred embodiment, the cell is a plant cell selected from the group consisting of: Arabidopsis; potato (i.e. Solanum tuberosum); tobacco (Nicotiana tabaccum); wheat; barley; maize and rice; Glycine max; Brassica napus. The term "transgenic cell" should be understood to mean a cell that comprises a transgene incorporated, ideally stably incorporated, into its genome. Generally, the transgene is exogenous material relative to the cell, or it may be endogenous to the cell but the cell is engineered to incorporate additional copies of the transgene.

In this specification, the term "plant" should be understood to mean a monocotyledon or dicotyledon plant. Preferably, the plant is a monocot plant. In one embodiment, the plant is from the Poaceae family or Arabidopsis genus. In one embodiment, the plant is from the Pooideae subfamily of grasses. In a particularly preferred embodiment, the plant is a cereal plant, typically a small grain cereal plant, preferably selected from the group consisting of: wheat; barley; maize; rice; potato (i.e. Solanum tuberosum); tobacco (Nicotiana tabaccum); Glycine max; Brassica napus.

In this specification, the term "recombinant construct" should understood to mean a polynucleotide construct designed to transfer exogenous genetic material into a target cell. They are sometimes referred to as vectors. The construct comprises a promoter region that is functional in a plant cell operably linked to an isolated polynucleotide of the invention. Preferably, the promoter is a DON-responsive promoter. Examples of DON-responsive promoters are the polynucleotide of SEQUENCE ID NO: 2, and functional variants thereof. The construct can comprise a number of sequence elements, including more than one coding sequence, promotors, and selectable markers. Typically, the construct or vector comprises a Ti plasmid (or a fragment thereof), suitably containing a region of T-DNA and ideally at least one or more virulence genes. Preferably, the Ti plasmid or fragment thereof is obtained from Agrobacterium. Suitably, the transgene is incorporated into the T-DNA region of the Ti plasmid. More preferably, the transgene is incorporated between the left and right borders of the T-DNA region. The Ti plasmid may comprise a selectable marker gene, although this is not required as successful transformation with the transgene may be rapidly detected for example by means of high-throughput PCR. When employed, the selectable marker gene is suitably contained within the T-DNA region and ideally operatively linked to the transgene.

The term "promoter region functional in a plant cell" refers to a polynucleotide sequence that is capable of driving expression of an operably linked transgene in a plant transformed with a recombinant construct comprising the promotor operably linked to the transgene. Generally, the promoter is capable of driving overexpression of the transgene. Examples of promoters include the maize ubiquitin promotor and the 35S Cauliflower Mosaic Virus promotor. Preferably, the promoter is a DON-responsive promoter. Ideally, the DON-responsive promoter comprises the polynucleotide of SEQUENCE ID NO: 2.

The term "DON-responsive promotor" refers to a promotor region that is functional in a plant cell and that is activated in response to the mycotoxin deoxynivalenol or DON analogs/derivatives. An example of a DON-responsive promotor is a promotor region comprising the polynucleotide of SEQUENCE ID NO: 2. Other examples of genes driven by DON-responsive promotors include glucosyltransferase and a multidrug resistance protein (Poppenberger et al., 2003; Walter et al., 2015).

In this specification, the term "transformation platform" should be understood to mean the genetic machinery required to transfer the transgene into a cell, and generally comprises an organism, for example a bacteria, capable of mediating cellular transformation and containing a recombinant construct of the invention. Examples of transformation platforms include *E. coli, A. tumefaciens, E. adhaerens*, and certain "transbacter" strains of bacteria. Other examples include: biolistic transformation and floral dipping.

In this specification, the term "transgene" should be understood to mean the isolated polynucleotide of the invention, and functional variants thereof.

In another embodiment of the invention, the transgene may facilitate the transfer of non-agronomic traits.

The term "operatively linked" should be understood to mean that in transformed cells the promoter will be transferred with the transgene and the transgene will be under the control of the promoter.

In this specification, the term "selectable marker" is taken to mean an exogenous piece of genetic material that when incorporated into the host DNA will confer a detectable signal of effective transformation. In a preferred embodiment, the selectable marker gene is selected from a group comprising: hph, neomycin phosphotransferase II [NPT II/Neo]), aadA and tetR. Appropriate reporter transgenes could include GUS or GFP.

In another embodiment, the transgene gene also functions as selectable marker gene, wherein the traits displayed by the transformed cell function as a selective marker for the successful incorporation of the transgene. For example the transgene may confer resistance to particular disease or antibiotic, wherein the transformed cell is identifiable by virtue of the fact that it is able to grow in conditions that would have previously not been viable. Typically, the antibiotic resistance is selected from resistance to antibiotics such as hygromycin, kanamycin, spectinomycin, tetracycline and ampicillin. Suitably the transgene confers resistance to disease including potato blight.

In a preferred embodiment, the transgene is not linked to selectable marker gene and detection of the successful incorporation of the transgene in the transformed plant is by means of PCR/high throughput genetic sequencing.

Preferably, the Ti plasmid contains one or more virulence genes, wherein the at least one virulence gene is typically selected from the group consisting of virA, virB, virC, virD, virE, virG, virK and virJ or functional variants thereof. Ideally, at least 6, 7 or 8 of the above virulence genes are contained on the transformation vector. Preferably, at least 6, 7 or 8 of the above virulence genes form part of the Ti plasmid. A functional variant of a virulence gene is a virulence gene that has been genetically modified by, for example, modification of one or more nucleotides, for example, in a process known in the art as "directed evolution".

Materials and Methods

DNA, RNA Extraction and cDNA Synthesis

DNA was extracted with the kit HP plant DNA mini kit (OMEGA) following manufacturer's instructions. RNA was extracted as described previously (Ansari et al. 2007) for the wheat heads or with the RNeasy plant kit (Qiagen) according to the manufacturer's instructions for the other plant tissues. DNase treatment of extracted total RNA was performed using the TURBO DNA-Free™ kit (Ambion Inc., USA), according to the manufacturer's instructions. The quality, yield and Integrity of the RNA was analysed by measuring the UV absorbance with a Nanodrop and after electrophoresis on an agarose gel. Absence of DNA contamination was confirmed by PCR. Reverse transcription of total RNA was performed as described previously (Walter et al. 2008).

Amplification and Sequencing of ENST1 mRNA

The mRNA sequence of ENST1 was obtained by three successive round of RACE (Rapid amplification of cDNA ends) using RNA extracted from DON-treated heads of wheat cv. CM82036 and the GeneRacer™ kit (Invitrogen). RNA was desphophorylated, decapped and reverse transcribed using SuperScript™ III RT (Invitrogen), according to manufacturer's instructions. Gene-specific primers are detailed in Supplemental table 1. The initial touchdown PCR reaction (50 µl volume final) contained 200 nM forward or reverse gene-specific primers (GSP1 primer), 600 nM of either 5' or 3' GeneRacer primer, 1× high Fidelity buffer, 2.5 U high fidelity platinum taq polymerase (Invitrogen), 2 mM MgSO4, 200 µM of each dNTP, 1 µl cDNA. PCR reaction conditions consisted of an initial denaturation step at 94° C. for 2 min followed by five cycles of at 94° C. for 30 s, 72° C. for 1 min; five cycles at 94° C. for 30 s, 70° C. for 1 min; 25 cycles at 94° C. for 30 s, final annealing at 68° C. for 30 s, one cycle 72° C. for 1 min. The two subsequent rounds of nested PCR (50 µl volume) contained 1 µl of a 1:300 dilution of the of nested PCR (50 µl volume) contained 1 µl of a 1:300 dilution of the previously amplified PCR product, 2.5 U LA Taq and 1× TaKaRa LA Taq™ $Mg^{2+}$ plus buffer (Takara, Japan), 200 µM dNTP (Gibco, UK), 200 nM of either the 5' or 3' nested GeneRacer primer and 200 nM of either the forward or reverse nested gene-specific primers (GSP2). PCR reaction conditions consisted of an initial denaturation at 94° C. for 1 min followed by 25 cycles of 94° C. for 30 s, 65° C. for 30 s and 68° C. for 2 min. The final extension was set at 68° C. for 10 min. Amplified fragments were cloned into the TOPO TA Cloning® kit (Invitrogen, UK) and sequenced.

Bioinformatic Analysis

Based on the sequences obtain from the RACE-PCR, the open reading frame (ORF) and the coding sequence (CDS) were deduced using NCBI's ORF finder (http://www.ncbi.nlm.nih.gov/go rf/gorf.html). Result was confirmed by analysis of the result obtain by BLASTn querying the cDNA sequences available in GenBank from the NCBI, the database KOMUGi (http://www.shigen.nig.ac.jp/wheat/komugi/), the genomic sequences from the International wheat genome sequencing consortium (http://wheat-urgi.versailles.inra.fr/Seq-Repository) and Draft genome assembly (http://www.cerealsdb.uk.net/cerealgenomics/CerealsDB).

All the sequence alignments and sequence analysis were performed with Multalin software (http://multalin.toulouse.inra.fr/multalin/multalin.html) and Bioedit (http://www.mbioncsu.edu/bioedit/bioedit.html). From this analysis the ORF cloned in this study was located on the wheat chromosome 4A and this variant was named TaENST1-4A. Homologous genes and the two other wheat variants (TaENST1-4B and TaENST1-4D) were deduced from analysis of the same database described above plus the International barley sequencing consortium (http://webblast.ipk-gatersleben.de/barley/viroblast.php) and the MIPS

*brachypodium* site (http://mips.helmholtz-muenchen.de/proj/plant/jsf/*brachypodium*/index.sp).

Cloning of the ENST1 Promotor Region & Generation of the Promoter: GUS Fusion.

Fragments of the promoter region (wheat cultivar CM82036) of the ENST1 gene were acquired using a Universal Genome Walker Kit (Clontech Laboratories, Inc., Palo Alto, Calif., USA). Using the Genome walker library, we prepared primary and nested PCR with the ENST1 gene-specific primer and the Advantage genomic polymerase mixture (Clontech, Palo Alto, Calif., USA). The gene specific primers were designed on the basis of the TaENST1 cDNA sequence. The nested PCR products were purified from 1.5% agarose gel, and subcloned into the pCRR2.1-TOPO vector (Invitrogen, Carlsbad, USA). The cloned vectors were then sequenced in Macrogen. To construct the ENST1 promoter:GUS plasmid, we amplified the promoter regions using the forward primer 5'GCTCTAGACTGC-CTCTTGCGAGCGGGAAG-3' (SEQ ID 4) and the reverse primer: 5'CAGGATCCCACTTCAG-GCACTCTCTCTTTCTGTG-3' (SEQ ID 5). All amplified DNA was sequenced and confirmed to be correct and then digested using Xba I-BamHI, and cloned into the pBI101.1 vector (Jefferson R A 1987).

Plant Material and Growth Conditions

*Arabidopsis thaliana* accession Columbia Col-0 was used in this study. Transgenic plants (Col-0) plants expressing ENST1 (the TaENST1-4A variant) coding sequence under the control of the CaMV 35S promoter were generated using a gateway cloning strategy (Primer sets listed in the supplemental table 1) using the pDONR207 (Invitrogen) and subsequently the pAM-PAT gateway vector as final vector (Bernoux et al. 2008). Transformation of *Arabidopsis* for either ENST1 expression or GUS expression under the control of the ENST1 promoter was carried out by the floral dipping method (Logemann et al. 2006) and selection of homozygous lines was achieved following the studies of resistance to BASTA (gene expression studies) or kanamucin resistance (promoter studies). Three independent homozygous transgenic lines were used for both the promoter fusion and the gene expressing studies. Plants were grown on a soil mix 2:2:1 (Multi-purpose Shamrock, John Innes compost No 2 and vermiculite) for seed production. After three days stratification in the dark at 4° C., the plants were grown in a growth chamber at 20-22° C. with a 16 h light/8 h dark photoperiod 70% humidity relative.

Wheat cultivar CM82036 is resistant to both FHB disease and DON treatment were kindly supplied by Dr. Hermann Buerstmayr (IFA Tulln, Austria). Adult plants were grown under contained environment conditions, as previously described (Ansari et al. 2007). At mid-anthesis (growth stage Zadoks 65) the heads were inoculated into the two central florets with either 15 µl of 5 mg/ml (i.e. 16.9 mM) DON (Santa Cruz) 0.02% Tween-20, 20 µl at $10^6$ conidia/ml of the fungus *F. graminearum* GZ3639 (WT) or GTZ40 (none DON producer) 0.02% Tween-20 or controls treatment (0.02% Tween-20). After inoculation heads were covered by plastic bags for 2 days. Treated spikelets were harvested at different time post-treatment indicated in the figure legend. For the time course experiment each time point corresponds to a pool of 4 heads each from individual plants. For the leaves treatment, the second leaves (growth stage Zadoks 10) were collected, placed in a square petri dish on moist Whatman No. 1 filter paper (Whatman, UK) soaked with 10 ml 0.67 mM benzimidazole and hold at their end with two slices of 1% agar 0.67 mM benzimidazole. Gently wounded leaves were treated with 10 µl 100 µg/ml of DON 0.02% Tween-20 and incubated in a growth chamber at 20-22° C. with a 16 h light/8 h dark photoperiod 70% humidity relative. For the roots treatment, seedling plants were germinated for 3 days at 20° C. on moist Whatman filter paper and then placed in a new Petri dish on Whatman filter paper soaked with 6 ml of either 20 µg/ml DON 0.02% Tween-20 (i.e. 67.5 µM) or 0.02% Tween-20 (controls). Germinating seedlings were incubated at 20° C. in the dark. For harvesting, all the different samples were flash-frozen in liquid N2 and stored at −70° C. prior to RNA extraction.

The wheat cv. Fielder and its' transgenic derivatives were used for the disease assessment studies. Transgenic wheat cv. Fielder overexpressing ENST was generated as follows. The ENST CDS was cloned using the gateway cloning strategy and the pDONR207 vector (Invitrogen); the gene was subsequently cloned into binary vector pSc4ActR1R2 (under the control of the rice actin promoter) (McElroy et al., 1990). The recombinant plasmid was then transformed into *Agrobacterium tumefaciens* strain AGL-1 and co-cultivated with immature wheat embryos at 23° C. in the dark for 2 days (Ishida et al., 2015). Following removal of the embryonic axis, subsequent tissue culture of the plant material was performed essentially as described previously (Risacher et al., 2009). DNA isolated from regenerated plantlets was analysed by qPCR to determine the copy number of the nptII selectable marker gene, relative to an internal control (Craze et al., in preparation). T0 transgenic plants carrying T-DNA (1 copy in lines OE-1 and OE-2; 1-2 copies in line OE-3) and overexpressing ENST were propagated to the T3 generation: plants were grown under contained environment conditions at 20-22° C. with a 16 h light/8 h dark photoperiod at 300 µmol m$^{-2}$ s$^{-1}$ 70% relative humidity, as previously described (Ansari et al., 2007). Homozygosity was analysed by testing for the presence-absence of the construct and calculating the segregation ratio in each generation. Transgenic lines OE-1, OE-2 and OE-3 were selected for *F. graminearum* studies on the basis that they respectively exhibited a 218, 445 and 80-fold increase in ENST gene expression, as compared to wild type plants.

Fungal Culture Inoculum

Asexual conidial inoculum (macroconidia) of *F. graminearum* wild type GZ3639 and the trichothecene-minus mutant derivative GZT40 (Proctor et al. 1995) was produced in Mung bean broth (Bai and Shaner 1996) and was harvested, washed and adjusted to $10^6$ conidia/ml, all as previously described (Brennan et al. 2005).

Real-Time and Semi Quantitative RT-PCR Analysis

Real-time RT-PCR (qRT-PCR) analyse was conducted using the Stratagene Mx3000™ Real-Time PCR. Each reaction was made with 1.25 µl of 1:5 (v/v) dilution of the first cDNA strand 0.2 µM each primers 1×SYBR® Premix Ex Taq™ (Tli RNase H plus, RR420A, Takara) in a total reaction volume of 12.5 µl, with the following conditions: 1 cycle of 1 min at 95° C.; 40 cycles of 5 s at 95° C. and 20 s at 60° C.; and a final cycle of 1 min at 95° C., 30 s at 55° C. and 30 s at 95° C. for the dissociation curve. Amplification specificity was verified by analysis of the dissociation curve and by visualisation of the amplification product size. The wheat Alpha-tubulin (gb: U76558.1) (Xiang et al. 2011) was used as a house keeping gene and verified to be not affected by the treatment used in our analysis and in the microarray expression data available (PLEXdb). All Real-time RT-PCR analysis were conducted in duplicate (two cDNA generated from independent Reverse transcriptions). The threshold cycle ($C_T$) values obtained by real-time RT-PCR were used to calculate the relative gene expression using the formula $2^{-(CT\ target\ gene - CT\ housekeeping\ gene)}$, as described previously (Livak and Schmittgen 2001).

For semi quantitative RT-PCR (sqRT-PCR), the template was calibrated by PCR amplification with the *Arabidopsis* Actin8 gene, and then the expression of the transgene was assayed with primer set matching with the CDS of TaENST1-4A. The thermal cycle parameters were 5 min 95° C.; 30 or 35 cycles at 45 s 95° C., 45 s 60° C., 45 s 72° C.; and a final extension of 5 min 72° C. PCR products were visualised after electrophoresis migration on 1.5% agarose gels under UV light after staining with the safeView nucleic acid staining (NBS-SV). Primer sets used are listed in the supplemental Table 1. The set of primers used for TaENST1-4A was designed to be specific to the chromosome 4A ENST1 variant and do not overlap with the gene fragment used for the VIGS. The specificity was verified by sequencing the corresponding product.

Virus-Induced Gene Silencing (VIGS)

The barley stripe mosaic virus (BSMV)-derived VIGS vectors used in this study consisted of the wild type BSMV ND18 α, β, γ tripartite genome (Scofield et al. 2005; Holzberg et al. 2002). VIGS analysis was used to silence ENST1, with 100% homology to TaENST1-4A but we cannot exclude that potentially the two other variant TaENST1-4B and TaENST1-4D were affected (each 91% homology). Fragment used for VIGS was amplified from the conserved domains of TaENST1-4A using the set of primers VIGS Pac1 for/VIGS Not1 rev (Table 1) and cloned into the pGEM-T vector (pGEM-T Easy cloning kit; Promega). Fragments were released by digestion with NotI and PacI, purified by gel extraction and ligated in the antisense orientation into NotI/PacI-digested BSMV γ vector, pSL038-1 (Scofield et al. 2005). The pSL038-1 plasmid harbouring the silencing fragment (BSMV:TaENST1) was verified by sequencing. A BSMV γ vector construct containing a 185 bp-fragment of the barley phytoene desaturase gene (BSMV:PDS) served as a positive control for VIGS and has been previously described (Scofield et al. 2005), silencing resulting in premature bleaching of plants (results not shown). The vectors containing the BSMV α, γ genomes without plant fragments (BSMV:00) or with BSMV:ENST1 and BSMV:PDS were linearised with MluI. The vector with BSMV β genome was linearized with SpeI. Capped in vitro transcripts were prepared from the linearized plasmids using the mMessage mMachine T7 in vitro transcription kit (AM1344, Ambion) following the manufacturer's protocol. Flag leaves of plants of wheat cv.CM82036 just before the emergence of the first wheat head were rub inoculated with BSMV constructs following the protocol described by (Scofield et al. 2005). Rub inoculations were done with 1:1:1 mixtures of the in vitro transcripts of BSMV α, β and γ RNA (BSMV:00) or derivatives γ RNA that contained plant fragments (BSMV:PDS or BSMV:TaENST1). At mid-anthesis two central spikelets of heads of BSMV infected plants were treated with DON or control (Mock treatment) as described above. The third spikelet above the treated spikelet was sampled 24 h post DON-treatment, flash frozen in liquid N2 and stored at −70° C. prior to silencing confirmation by real time RT-PCR analysis. The number of damaged (discoloured and necrosis) spikelets (including treated spikelets) was assessed at 14 days post DON inoculation. Sixteen spikelets (8 plants) were subjected to each treatment combination in each of two replica experiments.

Detached Leaf Disease Assessment Study

Detached leaf disease trials were performed as described previously (Browne and Cooke, 2004), using wheat cv. Fielder and transgenic lines overexpressing TaENST. An 8 cm section was cut from the second leaf of 3-leaf-stage plants (growth stage 13; (Zadoks et al., 1974)). Leaf sections were placed with the adaxial side facing upwards on the surface of a Petri dish (90 mm diameter). The cut ends were placed between a sandwich of 1% plant agar pH 5.7 (Duchefa) containing 0.5 mM benzimidazole (agar was removed from the centre of the plate to prevent excessive fungal growth at the point of leaf inoculation). The centre of each leaf section was punctured and treated with a 4 µl droplet of 0.02% Tween-20 (mock) or this solution augmented with either $10^6$ conidia/ml of *F. graminearum* strain GZ3639 or $10^6$ conidia/ml of strain GZ3639 plus 75 µM DON. Plates were incubated at 20° C. under a 16 h light/8 h dark cycle. Leaf sections were analysed 4 days post-inoculation. Disease leaf area was estimated using FIJI software of photographed leaf sections (Schindelin et al., 2012). Leaf sections were dipped in water and vigorously vortexed and macroconidia production were counted using a haemocytometer (Hycor Biomedical). There were three biological replicates, each including 6 plates per treatment, and each plate including two leaf sections per wheat genotype.

FHB Assessment and DON Studies on t

Wheat cv. Fielder and transgenic lines overexpressing TaENST were grown and heads were treated as described above (VIGS) with 20 µl of $10^6$ conidia/ml of *F. graminearum* strain GZ3639 or Tween-20 (mock) (FHB experiment). The level of infection was calculated by visually scoring the number of infected spikelets at 7, 14 and 21 days post inoculation and data were used to calculate area under the disease progress curve (AUDPC) (Shaner, 1977). There were three biological replicates, each including at least 20 heads (10 plants) per treatment.

Root Hair Assay

The root hair assay was conducted as previously described (Kacprzyk et al. 2014). Briefly, five days old seedling were treated with 65 µM SA solution and incubated at 22° C. in constant light until scoring. The Apostosis-Like Program Cell Death (AL-PCD) was assessed by scoring root hair viability with a fluorescein diacetate (FDA) staining and examination under the microscope of the emission of the fluorescein when excited at the wavelength 485 nm. Root hairs negative for FDA staining were examined further and scored as programmed cell death (PCD) when having a condensed cell content and protoplast retracted away from the cell wall (as opposed to necrotic cells which have no retracted cytoplasm and therefore no distinguishable morphology compared to living cells under the light microscope). The percentage for each category was calculated as a percentage of the total number of root hair scored (about 100) averaged over at least three replicates.

GUS Analysis

Seedlings were incubated in DON or mock treatment as previously described (Poppenberger et al. 2003) and the GUS staining was conducted at various time points post-incubation in mock or DON treatment. Histochemical staining were conducted according to published method (Jefferson R A 1987).

Statistical Analysis

All the statistical analysis was performed using the SPSS statistic version 20 software (SPSS). The normality of the data distribution was evaluated with the Shapiro-Wilk test. In the case of the gene expression, conidial production, DON and *Fusarium* head blight data sets, individual treatments were compared using either the Mann-Whitney U or Kruskal-Wallis test. The normally-distributed infected leaf area data from detached leaf experiment was assessed by ANOVA incorporating Tukey's HSD test at the 0.05 level of significance.

Results

Analysis of ENST1

Using a RACE-PCR approach we cloned the ENST1 ORF from the wheat cultivar CM82036. Bioinformatics analyses show that the deduced CDS share 100% nucleotide homology with a sequence in the Chinese spring chromosome 4A. As the result we designated this gene as TaENST1-4A. Two other variants present in the wheat genome located on Chinese Spring chromosome 4B (TaENST1cs-4B) and 4D (TaENST1cs-4D) were identified sharing high homology with TaENST1-4A (FIG. 1). Further analyses show that TaENST1-4A sequence shared no significant homology with any characterised gene or protein. Homologs of TaENST1-4A were found only within the Poaceae family (Wheat, Barley, *Festuca*, *Aegilops* and *Brachypodium*) (FIG. 2A). At the protein level TaENST1-4A shared ≥90% identity with the two other wheat variants and *Aegilops tauschii*, 87% with Barley, 67% with *Festuca* and 45% with *Brachypodium* (FIG. 2B).

Effect of ENST1 on Programmed Cell Death

Figure 3:
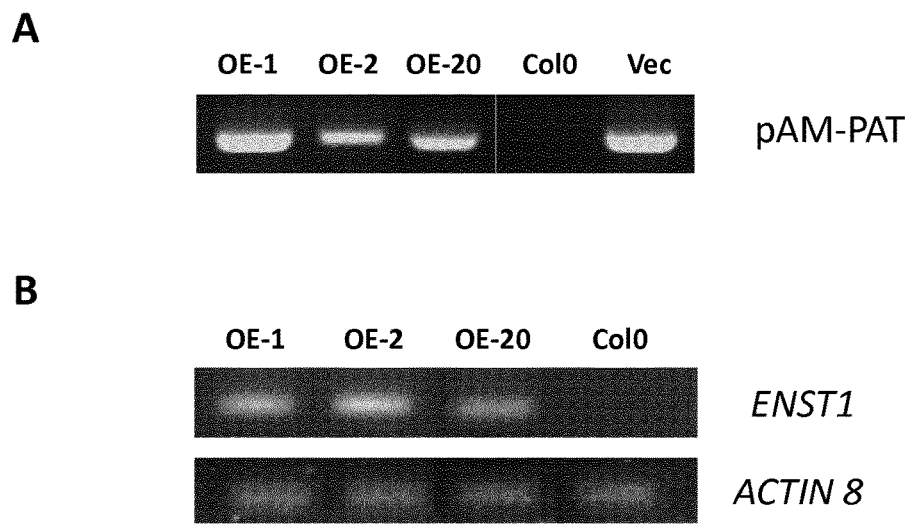

In order to understand how ENST1 participate to DON resistance, *Arabidopsis thaliana* transgenic lines expressing ENST1 conserved domains under the control of the CaMV 35S promoter were generated using the pAM-PAT vector (note there is no endogenous ENST1 homolog in *Arabidopsis*). Three independent homozygous lines named OE-1, OE-2 and OE-20 were used in this study. First characterised to verify the presence of the T-DNA by PCR (FIG. 3A), the transgenic lines were then confirmed for the correct ENST1 over-expression by RT-PCR (FIG. 3B). These ENST1-expressing lines exhibit no morphological or developmental alteration under normal plant growth conditions (data not shown).

Exogenous application of SA induced programmed cell death (PCD) in different plants and tissues, like the root hair in *Arabidopsis*. The root hair assay was used to test if the PCD induced by SA was altered in the ENST1-expresser. In condition control (water treatment) the cell death in root hair was measured after one day post treatment and showed a basal level of PCD with no difference between the different plants (FIG. 4). After SA treatment significant inductions of PCD was observed in the WT plants. But SA induced significantly higher PCD in plants expressing ENST1 (FIG. 4). ENST1 expression did not enhance cell death induced by heat (FIG. 4), indicating that it is not a general effect on cell death, but rather specific to particular treatments, including at least salicylic acid.

Characterisation of the ENST1 Promoter and Gene Expression

To confirm that ENST1 was responsive to the toxin DON, a real time RT-PCR assay (specific to TaENST1-4A) was used to measure the level of gene expression in different wheat tissues treated with the toxin. The basal expression of ENST1 in mock-treated samples was very low or nearly non detectable, on the contrary a high expression was observed in all the tissues treated with the toxin (FIG. 5A). In order to determine if ENST1 gene expression was induced by the deoxynivalenol producer *Fusarium graminearum* (strain GZ3639), the level of expression was measured in spikelets infected with the fungus during the first few days post-fungal inoculation. The results showed that the ENST1 is early induced at 1 day post inoculation (dpi); with a peak of induction at 2 dpi, following by a return at a basic level (FIG. 5B). In the same experiments, we analysed the effect of the DON-non-producing mutant derivative of GZ3639, namely GZT40, on ENST1 expression. The induction of ENST1 expression by GZT40 was very low at all the days post inoculation (FIG. 3B). Thus we conclude that ENST1 is a component of the early host response to toxin production by *Fusarium* fungi. Transgenic plants expressing the GUS gene under the control of the ENST1 promoter (upstream sequence) were stained for GUS activity post incubation in either DON or mock-treatment. As seen in FIG. 6, activity was both DON and tissue-dependent.

TaENST Enhances Wheat Leaf Resistance to *F. graminearum*

Using a detached leaf assay, the spread and sporulation of *F. graminearum* (strain GZ3639) on transgenic lines OE-1, OE-2 and OE-3 overexpressing TaENST was evaluated, relative to wild type plants. Disease and sporulation were reduced in the overexpressor as compared to wild type plants. Thus, the overexpression of TaENST enhanced wheat resistance to colonisation by *F. graminearum*. (FIG. 8)

Overexpression of TaENST Retards the Spread of FHB Disease Symptoms

The effect of TaENST overexpression on the spread of FHB symptoms from inoculated central spikelets of wheat heads was evaluated. Results showed that wild type cv. Fielder had an average of 5.1 diseased spikelets at 21 days post-treatment. All three transgenic lines exhibited less disease spread; significant reductions of 23 and 17% were respectively observed for OE-1 and OE-2, relative to wild type plants. The reduction observed for OE-3 at 21 days post-treatment was not significant, however, like OE1, the disease progression for line OE3 (evaluated as AUDPC calculated using disease scores from 7, 14 and 21 dpi) was significantly lower than on wild type plants (WT). Overall, the results demonstrated that overexpression of TaENST provided quantitative resistance to FHB. (FIG. 9)

The Role of ENST1 in DON Resistance

We used virus-induced gene silencing (VIGS) to test the hypothesis that ENST1 plays a role in resistance to DON in wheat. We treated plants with a VIGS construct targeting either ENST1 or PDS (positive control) or no gene (negative control) for silencing. Constructs were applied to the flag leaves of the toxin-resistant wheat cv. CM82036 before emergence of the primary head. Around two weeks later, two central spikelets were treated with DON (16.9 mM) or mock 0.2% Tween20 treatment at mid anthesis. At 1 dpi, one spikelet above the one which had been treated was removed and used to measure the expression level of ENST1 (the TaENST1-4A variant) using real-time RT-PCR. As shown previously very low ENST expression was observed in the non-toxin treated plants (mock), whether in the control (BSMV:00) or silenced plants (BSMV:ENST1) (FIG. 7A). ENST1 was induced 43-fold by DON in the mock BSMV: 00-treated plants. However, silencing of ENST1 due to BSMV:TaENST1 plants treatment reduced the DON induction by 77% (as compared to Don-treated, BSMV:00-treated plants) (FIG. 7A). These shows that gene silencing of ENST1 was effective in DON-treated wheat heads. We measured the phenotypic effect of DON on plants at 14 days post-toxin treatment. Plants treated with BSMV:TaENST1 were more sensitive to DON-induced damage of spikelets than the non-silenced plants BSMV:00 (FIGS. 7B & 7C). The numbers of ENST1 silenced spikelets showing DON-induced damage was significantly greater than for the BSMV:00 treatment (2.5 fold increase). Thus indicates a direct role of ENST1 in DON resistance.

TABLE 1

Primers used in this study.

| Primer ID | Sequence (5' to 3') | Purpose |
|---|---|---|
| TaENST1-GSP1 for | CACACACAGAAAGAGAGAGTGCCTGAAGTG (SEQ ID 6) | RACE-PCR cloning |
| TaENST1-GSP1 rev | CCCTTCGTCCATAGGCTTGTTAGAATCG (SEQ ID 7) | |
| TaENST1-GSP2 for | GCAAGCAACAAGGAGGAGAGCGAGAAGAAT (SEQ ID 8) | |
| TaENST1-GSP2 rev | GATTCTTCTCGCTCTCCTCCTTGTTGCT (SEQ ID 9) | |
| TaENST1-GSP3 for | GAAGCAGCACAAAATGGTAAAAGAGGTGAA (SEQ ID 10) | |
| TAENST1-GSP3 rev | GGCACTCTCTCTTTCTGTGTGTGTGTGT (SEQ ID 11) | |
| VIGS PAC1 for | CGATTAATTAAATGGTGTGGTCTACCAGCAAG (SEQ ID 12) | VIGS cloning |
| VIGS NOT1 rev | CGAGCGGCCGCCATCAGAACCGGAATCAACG (SEQ ID 13) | |
| TaENST1 M1 For GWY | GGAGATAGAACCATGGTGTGGTCTACCAGCAAG (SEQ ID 14) | pDONR207 cloning |
| TaENST1 Stop Rev GWY | CAAGAAAGCTGGGTCTCAACTGAATATTTTGTAGAATTTCC (SEQ ID 15) | |
| pAMPAT-35S for | CCTTCGCAAGACCCTTC (SEQ ID 16) | primer vector |
| pAMPAT-TER rev | GATTTGTAGAGAGAGACTGG (SEQ ID 17) | pAMPAT |
| TaENST1-CDS for | GACGAAGATCGAGGCTGTTCGGA (SEQ ID 18) | sqRT-PCR |
| TaENST1-CDS rev | GAATTTCCTAGAGCTGATCTTATGG (SEQ ID 19) | |
| AtACTIN-8 for | ACCCGAGAGGAAGTACAGTG (SEQ ID 20) | sqRT-PCR |
| AtACTIN-8 rev | ATACTCTGCCTTAGAGATCCACA (SEQ ID 21) | |
| TaENST1-3'UTR for | TATGGGATCTCGAGGACTGG (SEQ ID 22) | qRT-PCR |
| TaENST1-3'UTR rev | TTGCCCAAAACGTAATAATGA (SEQ ID 23) | |
| TaAlpha-tubulin for | ATCTCCAACTCCACCAGTGTCG (SEQ ID 24) | qRT-PCR |
| TaAlpha-tubulin rev | TCATCGCCCTCATCACCGTC (SEQ ID 25) | |

REFERENCES

Ansari K I, Walter S, Brennan J M, Lemmens M, Kessans S, McGahern A, Egan D, Doohan F M (2007) Retrotransposon and gene activation in wheat in response to mycotoxigenic and non-mycotoxigenic-associated *Fusarium* stress. Theoretical and Applied Genetics 114 (5):927-937

Bai G-H, Shaner G (1996) Variation in *Fusarium graminearum* and cultivar resistance to wheat scab. Plant Disease 80 (9):975-979

Bernoux M, Timmers T, Jauneau A, Brière C, de Wit P J, Marco Y, Deslandes L (2008) RD19, an *Arabidopsis* cysteine protease required for RRS1-R-mediated resistance, is relocalized to the nucleus by the *Ralstonia solanacearum* PopP2 effector. The Plant Cell Online 20 (8):2252-2264

Brennan J, Egan D, Cooke B, Doohan F (2005) Effect of temperature on head blight of wheat caused by *Fusarium culmorum* and *F. graminearum*. Plant pathology 54 (2): 156-160

Delaney T P, Uknes S, Vernooij B, Friedrich L, Weymann K, Negrotto D, Gaffney T, Gut-Rella M, Kessmann H, Ward E (1994) A central role of salicylic acid in plant disease resistance. Science 266 (5188):1247-1250

Görlach J, Volrath S, Knauf-Beiter G, Hengy G, Beckhove U, Kogel K-H, Oostendorp M, Staub T, Ward E, Kessmann H (1996) Benzothiadiazole, a novel class of inducers of systemic acquired resistance, activates gene expression and disease resistance in wheat. The Plant Cell Online 8 (4):629-643

Holzberg S, Brosio P, Gross C, Pogue G P (2002) Barley stripe mosaic virus-induced gene silencing in a monocot plant. The Plant Journal 30 (3):315-327

Jefferson R A KTAaBMW (1987) GUS fusions: beta-glucuronidase as a sensitive and versatile gene fusion marker in higher plants. The Embo Journal 6:7

Kacprzyk J, Devine A, McCabe P F (2014) The Root Hair Assay Facilitates the Use of Genetic and Pharmacological Tools in Order to Dissect Multiple Signalling Pathways That Lead to Programmed Cell Death. PloS one 9 (4): e94898

Lawton K A, Friedrich L, Hunt M, Weymann K, Delaney T, Kessmann H, Staub T, Ryals J (1996) Benzothiadiazole induces disease resistance in *Arabidopsis* by activation of the systemic acquired resistance signal transduction pathway. The Plant Journal 10 (1):71-82

Livak K J, Schmittgen T D (2001) Analysis of Relative Gene Expression Data Using Real-Time Quantitative PCR and the $2^{-\Delta\Delta CT}$ Method. methods 25 (4):402-408

Logemann E, Birkenbihl R P, Ülker B, Somssich I E (2006) An improved method for preparing *Agrobacterium* cells that simplifies the *Arabidopsis* transformation protocol. Plant Methods 2 (1):16

Makandar R, Nalam V J, Lee H, Trick H N, Dong Y, Shah J (2012) Salicylic acid regulates basal resistance to *Fusarium* head blight in wheat. Molecular Plant-Microbe Interactions 25 (3):431-439

Poppenberger B, Berthiller F, Lucyshyn D, Sieberer T, Schuhmacher R, Krska R, Kuchler K, Glössl J, Luschnig C, Adam G (2003) Detoxification of the *Fusarium* mycotoxin deoxynivalenol by a UDP-glucosyltransferase from *Arabidopsis thaliana*. Journal of Biological Chemistry 278 (48):47905-47914

Proctor R H, Hohn T M, McCormick S P (1995) Reduced virulence of *Gibberella zeae* caused by disruption of a trichthecine toxin biosynthetic gene. MPMI-Molecular Plant Microbe Interactions 8 (4):593-601

Scofield S R, Huang L, Brandt A S, Gill B S (2005) Development of a virus-induced gene-silencing system for hexaploid wheat and its use in functional analysis of the Lr21-mediated leaf rust resistance pathway. Plant Physiology 138 (4):2165-2173

Vlot A C, Dempsey D M A, Klessig D F (2009) Salicylic acid, a multifaceted hormone to combat disease. Annual review of phytopathology 47:177-206

Walter S, Brennan J M, Arunachalam C, Ansari K I, Hu X, Khan M R, Trognitz F, Trognitz B, Leonard G, Egan D (2008) Components of the gene network associated with genotype-dependent response of wheat to the *Fusarium* mycotoxin deoxynivalenol. Functional & integrative genomics 8 (4):421-427

Walter S, et al. (2015) A wheat ABC transporter contributes to both grain formation and mycotoxin tolerance. *Journal of Experimental Botany.*

White R (1979) Acetylsalicylic acid (aspirin) induces resistance to tobacco mosaic virus in tobacco. Virology 99 (2):410-412

Xiang Y, Song M, Wei Z, Tong J, Zhang L, Xiao L, Ma Z, Wang Y (2011) A jacalin-related lectin-like gene in wheat is a component of the plant defence system. Journal of experimental botany 62 (15):5471-5483

The invention claimed is:

1. A recombinant construct comprising a promoter region functional in a plant cell operably linked to a transgene, wherein the transgene comprises an isolated polynucleotide having a sequence selected from the group consisting of SEQ ID NO: 1, SEQ ID NO: 26, SEQ ID NO: 27, SEQ ID NO: 28, SEQ ID NO: 31, SEQ ID NO: 32, SEQ ID NO: 33, and SEQ ID NO: 34, and wherein the promoter region comprises a deoxynivalenol-responsive promoter.

2. A recombinant construct as claimed in claim 1 in which the promoter region comprises SEQ ID NO: 2.

3. A transformation platform comprising an organism capable of mediating cellular transformation and including a recombinant construct of claim 1.

4. A transformation platform as claimed in claim 3 in which the organism is a bacterium.

5. A transformation platform as claimed in claim 3 in which the promoter region comprises SEQ ID NO: 2 and the transgene comprises an isolated polynucleotide having the sequence of SEQ ID NO: 1.

6. A plant material genetically transformed with a recombinant construct of claim 1.

7. A plant material as claimed in claim 6 and selected from a plant cell, plant cell culture, plant tissue, plant, and transgenic plant seed.

8. A recombinant construct as claimed in claim 1, wherein the transgene comprises an isolated polynucleotide having a sequence selected from the group consisting of SEQ ID NO: 1, SEQ ID NO: 26, SEQ ID NO: 27, and SEQ ID NO: 28.

9. A recombinant construct as claimed in claim 8 in which the promoter region comprises SEQ ID NO: 2.

* * * * *

SEQUENCE LISTING

```
<160> NUMBER OF SEQ ID NOS: 43

<210> SEQ ID NO 1
<211> LENGTH: 393
<212> TYPE: DNA
<213> ORGANISM: Triticum aestivum

<400> SEQUENCE: 1
atggtgtggt ctaccagcaa gcaacaagga ggagagcgag aagaatcgaa gcagcacaaa      60
atggtaaaag aggtgaagac acctatcttc acgcatcagc tctccttcca ttctcttccc     120
cttaacaaag tcaagaacat cgaggtcgac cgcttgaggc tgtctttcac gacgccgaaa     180
aattctacgc tggtccccgt tgattccggt tctgatgaag agagtgacga agatcgaggc     240
tgttcggaca tcgattctaa caagcctatg gacgaagggt tagatcacat ctgtagtggt     300
ctgcatgcta ttccccggaa aaacaaagca agatcggcca agaaaagatc ccataagatc     360
agctctagga aattctacaa aatattcagt tga                                  393

<210> SEQ ID NO 2
<211> LENGTH: 1277
<212> TYPE: DNA
<213> ORGANISM: Triticum aestivum

<400> SEQUENCE: 2
ctgcctcttg cgagcgggaa gccagtgcca ccgctcggca tttcccgtac atccggatct      60
aagctcaccc gtagcgcgac aattagtgga taggagttgg ggcctcaccg agaagcactg     120
cccttcctgg tcctcctacc tgcaaagagg tgaagatgcg gtcggccgca ccgcggtagc     180
tcgacggctc cgtgaatggt ggggcagatg ccacgttgct gcatggctcc gcgcgactgs     240
cmacatgaat ggtggcgacg ggtacgaaag tggcggcagc tacaacttcg cgccgacatg     300
agtatcccga gcctccttcg ccgtctcgtg caccttttt taacaaatta agaagctttt      360
tgcccttctg ggatactgct gggcccgagg cggagtgaat ctgggcgggt tgggtacaac     420
catacaagga ggaagaatgt gggagtagtg gggtggttga cctgcttttc ttcggttcag     480
ttcgctcctg ttcaaaagaa tgaccaacta ggagaaaaaa ccaaaagcaa aaataaactg     540
tcaacgtggc aagcgctaaa attgagagaa gaaaaaccaa gttaaaatgt aaacacgagg     600
gtaaaatgtg gcacaaagtg caaagtgaa ggtactcacc tgccaaaatg aaagtgaagg     660
tgctccctcc ttcccaaaat ataaggcgcg gattgacttt tctggtcttt attgtgcaac     720
tttgactata attttcatgt attcgttaca agacaaatac gatgatgcca tttatacata     780
ttcaatcaat atactttgat atatattaat ggtcaaagtc gtgcataaaa aaccgcctta     840
tattttagga aagaggaagt ataaattaag gattttctcc gggttaaatg aaattaactc     900
```

```
ttattttatt aatgtccaca ccggaggcct cccccttgtt agaatcctga ctccatccct    960
gatcacggct gtccggttgg atgcccacca aggcattttt cctctccccg tacatgtgca   1020
aatggatagc gaccttggca accaagaaaa tggatatcga caagattcgt cagacgagtc   1080
agcgacgaag aaccttggca accaaggcgc gcggcagcca ccgtgacgat caagtcaaat   1140
aatcatctga cctcgtgctt ccgctcacat ccgtcgtttt cgtcctggac gaaccttcac   1200
gcagctttct cccctcagct tctctctctt cgcccctcac aacttatata taagtgtcgc   1260
actactagat cctcaac                                                  1277
```

<210> SEQ ID NO 3
<211> LENGTH: 130
<212> TYPE: PRT
<213> ORGANISM: Triticum aestivum

<400> SEQUENCE: 3

```
Met Val Trp Ser Thr Ser Lys Gln Gln Gly Gly Glu Arg Glu Ser
1               5                   10                  15

Lys Gln His Lys Met Val Lys Glu Val Lys Thr Pro Ile Phe Thr His
                20                  25                  30

Gln Leu Ser Phe His Ser Leu Pro Leu Asn Lys Val Lys Asn Ile Glu
            35                  40                  45

Val Asp Arg Leu Arg Leu Ser Phe Thr Thr Pro Lys Asn Ser Thr Leu
50                  55                  60

Val Pro Val Asp Ser Gly Ser Asp Glu Glu Ser Asp Glu Asp Arg Gly
65                  70                  75                  80

Cys Ser Asp Ile Asp Ser Asn Lys Pro Met Asp Glu Gly Leu Asp His
                85                  90                  95

Ile Cys Ser Gly Leu His Ala Ile Pro Arg Lys Asn Lys Ala Arg Ser
            100                 105                 110

Ala Lys Lys Arg Ser His Lys Ile Ser Ser Arg Lys Phe Tyr Lys Ile
        115                 120                 125

Phe Ser
    130
```

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4

```
gctctagact gcctcttgcg agcgggaag                                       29
```

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5

```
caggatccca cttcaggcac tctctctttc tgtg                                 34
```

<210> SEQ ID NO 6
<211> LENGTH: 30
<212> TYPE: DNA
<213> ORGANISM: Artificial Sequence
<220> FEATURE:

<223> OTHER INFORMATION: primer

<400> SEQUENCE: 6
cacacacaga aagagagagt gcctgaagtg                                30

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
cccttcgtcc ataggcttgt tagaatcg                                  28

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gcaagcaaca aggaggagag cgagaagaat                                30

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
gattcttctc gctctcctcc ttgttgct                                  28

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
gaagcagcac aaaatggtaa aagaggtgaa                                30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
ggcactctct ctttctgtgt gtgtgtgtgt                                30

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
cgattaatta aatggtgtgg tctaccagca ag                             32

```
<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
cgagcggccg ccatcagaac cggaatcaac g                              31

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ggagatagaa ccatggtgtg gtctaccagc aag                            33

<210> SEQ ID NO 15
<211> LENGTH: 41
<212> TYPE: DNA
<213> ORGANISM: Artificial Sequence
<220> FEATURE:
<223> OTHER INFORMATION: primer

<400> SEQUENCE: 15
caagaaagct gggtctcaac tgaatatttt gtagaatttc c                   41

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
ccttcgcaag acccttc                                              17

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gatttgtaga gagagactgg                                           20

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gacgaagatc gaggctgttc gga                                       23

<210> SEQ ID NO 19
<211> LENGTH: 25
<212> TYPE: DNA
<213> ORGANISM: Artificial Sequence
<220> FEATURE:
<223> OTHER INFORMATION: primer
```

<400> SEQUENCE: 19
gaatttccta gagctgatct tatgg                                    25

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
acccgagagg aagtacagtg                                          20

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
atactctgcc ttagagatcc aca                                      23

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tatgggatct cgaggactgg                                          20

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ttgcccaaaa cgtaataatg a                                        21

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
atctccaact ccaccagtgt cg                                       22

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
tcatcgccct catcaccgtc                                          20

<210> SEQ ID NO 26
<211> LENGTH: 393

```
<212> TYPE: DNA
<213> ORGANISM: Triticum aestivum

<400> SEQUENCE: 26
atggtgtggt ctaccagcaa gcaacaagga ggagagcgag aagaatcgaa gcagcacaaa      60
atggtaaaag aggtgaagac acctatcttc acgcatcagc tctccttcca ttctcttccc     120
cttaacaaag tcaagaacat cgaggtcgac cgcttgaggc tgtctttcac gacgccgaaa     180
aattctacgc tggtccccgt tgattccggt tctgatgaag agagtgacga agatcgaggc     240
tgttcggaca tcgattctaa caagcctatg gacgaagggt tagatcacat ctgtagtggt     300
ctgcatgcta ttccccggaa aaacaaagca agatcggcca agaaaagatc ccataagatc     360
agctctagga aattctacaa aatattcagt tga                                  393

<210> SEQ ID NO 27
<211> LENGTH: 435
<212> TYPE: DNA
<213> ORGANISM: Triticum aestivum

<400> SEQUENCE: 27
atggtgtggt ctacgagcaa gcaacaagga ggagatcaag aagaacccaa gcagcacaaa      60
atggtaaaag aggtgaagaa gagtgagaca cccatcttca cgtatcagct cccccttccat    120 tctctttccc ttaacaaagt caagaacatc gaggtcgacc gcttgaggct gtccttcacg     180
acggcgaaaa actctacgct ggtccccgtt gattccggtt ctgatgaaga gagtgacgaa     240
gatcaaggct gttcggacat cgacgacact gtaaacagta taggtggaca aatgaccgtc     300
gataagccta tggacgaagg gttagatcgc atctgtagtg gtctgcatgc tattcccagg     360
aaaaataaag caagatcggc caagaaaaga tcccataagc tcagctctag gaagttctac     420
aaaatattca gctga                                                      435

<210> SEQ ID NO 28
<211> LENGTH: 402
<212> TYPE: DNA
<213> ORGANISM: Triticum aestivum

<400> SEQUENCE: 28
atgatgtggt cttcgagcaa gcaacaagga ggagaccgag aagaatggaa gcagcacaag      60
atggtaaaag aggtgaagaa gagtgagaca cccatcttca cgtatcagct cccccttccat    120 tctctccccc ttaacaaagt caagaacatc gaggtcgacc gcctgaggct gtccttcacg     180
acgccgaaaa attctacgct ggtccccgtt gattccggtt ctgatgaaga gagtgacgaa     240
gatcaaggct gttcggacat cgattctgat aagcctatgg acgaagtgtt agatcacatc     300
tgttgtggtc tgcatgctat tccccggaaa aataaagcaa gatcggccaa gaaaagatcc     360
cacaagctca gctctaggaa attctacaaa atattcagct ga                        402

<210> SEQ ID NO 29
<211> LENGTH: 393
<212> TYPE: DNA
<213> ORGANISM: Triticum aestivum

<400> SEQUENCE: 29
atggtgtggt ctaccagcaa gcaacaagga ggagagcgag aagaatcgaa gcagcacaaa      60
atggtaaaag aggtgaagac acctatcttc acgcatcagc tctccttcca ttctcttccc     120
cttaacaaag tcaagaacat cgaggtcgac cgcttgaggc tgtctttcac gacgccgaaa     180
```

```
aattctacgc tggtccccgt tgattccggt tctgatgaag agagtgacga agatcgaggc      240
tgttcggaca tcgattctaa caagcctatg gacgaagggt tagatcacat ctgtagtggt      300
ctgcatgcta ttccccggaa aaacaaagca agatcggcca agaaaagatc ccataagatc      360
agctctagga aattctacaa aatattcagt tga                                   393

<210> SEQ ID NO 30
<211> LENGTH: 401
<212> TYPE: DNA
<213> ORGANISM: Artificial Sequence
<220> FEATURE:
<223> OTHER INFORMATION: Consensus sequence

<400> SEQUENCE: 30
atggtgtggt ctacgagcaa gcaacaagga ggagacgaga agaatcgaag cagcacaaaa       60
tggtaaaaga ggtgaagaag agtgagacac ccatcttcac gtatcagctc cccttccatt      120
ctcttcccct taacaaagtc aagaacatcg aggtcgaccg cttgaggctg tccttcacga      180
cgccgaaaaa ttctacgctg gtcccgttg attccggttc tgatgaagag agtgacgaag       240
atcaaggctg ttcggacatc gattctgata agcctatgga cgaagggtta gatcacatct      300
gtagtggtct gcatgctatt ccccggaaaa ataaagcaag atcggccaag aaaagatccc      360
ataagctcag ctctaggaaa ttctacaaaa tattcagctg a                          401

<210> SEQ ID NO 31
<211> LENGTH: 399
<212> TYPE: DNA
<213> ORGANISM: aegilops tauschii

<400> SEQUENCE: 31
atgtggtctt cgagcaagca acaaggagga gaccgagaag aatggaagca gcacaagatg       60
gtaaaagagg tgaagaagag tgagacaccc atcttcacgt atcagctccc cttccattct      120
ctccccctta caaagtcaa gaacatcgag gtcgaccgcc tgaggctgtc cttcacgacg       180
ccgaaaaatt ctacgctggt ccccgttgat tccggttctg atgaagagag tgacgaagat      240
caaggctgtt cggacatcga ttctgataag cctatggacg aagtgttaga tcacatctgt      300
tgtggtctgc atgctattcc cggaaaaaat aaagcaagat cggccaagaa aagatcccac      360
aagctcagct ctaggaaatt ctacaaaata ttcagctga                             399

<210> SEQ ID NO 32
<211> LENGTH: 429
<212> TYPE: DNA
<213> ORGANISM: Hordeum vulgare

<400> SEQUENCE: 32
atgatggtgt ggtctacgag caagcaacaa ggaggagatc gagcagaatc gaagcagcac       60
aaaatggtaa aagagatgaa gagtagcgag acacctacct tcacgtatca gctccccttc      120
cattctcttt cccttaacaa agtcaagaac atcgaggtcg accgcttgag gctgtccttc      180
acaacgccga aacacagtac gctggtcccc gttgattccg attctgatga agagagtgac      240
gactgttcgg acattgatca cgctgtaaac agcacaggtg ggcaaatggc cgccgacaag      300
cctgtggatg cagggttaga tcacatctgt agtggtctgc atgccattcc ccggaagaat      360
aaagctagat cggccaagaa aagatcccac aagctcagct ctaggaaatt ttacaaaata      420
ttcagttga                                                              429
```

```
<210> SEQ ID NO 33
<211> LENGTH: 366
<212> TYPE: DNA
<213> ORGANISM: Festuca pratensis

<400> SEQUENCE: 33
atggtgtggc ctgcgagcaa gcaacaaggt ggaggagatc gaccagaagc gaagcaccac    60
aatacggtga aggaggtgaa gagtgggaca ccaattttta cgtatcagct ccccttacat   120
tccctttccc ttaacaaagt caagaacatc gaggttgacc gcttgaggct gtccttcgcg   180
accccgcgaa agccagcgct ggtccccgtt gattctgatg atgaggagag ccacgacgat   240
caagagtgct tggatcacat ctgtagtgcc gccatgcatg ctgttcctcg aagaataaa    300 tcaagatcga ccaagaagag agtccgcaag gccagctata aggaatacta caagatattc   360
agttga                                                              366

<210> SEQ ID NO 34
<211> LENGTH: 396
<212> TYPE: DNA
<213> ORGANISM: Brachypodium distachyon

<400> SEQUENCE: 34
atgacctgca ttggaggaga tcatggagaa gtgaagcagc agcagaaggt ggcggcacag    60
agtaaaaatg ccgggttgat tcagctgaag acgaagaaga gcgaggatcc tatgttggtg   120
catcaattcc ccttccatga tctctcgctt aacaaagtca gaacatcga ggtggaccgt    180 ttgaggctat ctccggtgac accgaaaaag ctgacatcgg caacggctga ttctgctgaa   240
gagaatcatg aggatcagga ccctgagacg ctcaaaaccg atgagagatt agatcagatg   300
tgtagttttc tacatgctat tccccgtaaa aacagatcga atcgagcaa gagaagaact    360 cagaagacca gctctaggaa actttgcagg ttctga                             396

<210> SEQ ID NO 35
<211> LENGTH: 382
<212> TYPE: DNA
<213> ORGANISM: Artificial Sequence
<220> FEATURE:
<223> OTHER INFORMATION: CONSENSUS SEQUENCE

<400> SEQUENCE: 35
atggtgtggt ctcgagcaag caacaaggag gagatcgaga aacgaagca gcacaaatgg     60 taaaagaggt gaagaagagt gagacaccat cttcacgtat cagctcccct tccattctct   120
ttcccttaac aaagtcaaga acatcgaggt cgaccgcttg aggctgtcct tcacgacgcc   180
gaaaaactac gctggtcccc gttgattccg ttctgatgaa gagagtgacg agatcaagct   240
gttcggacat cgaaaagcct tggagaaggg ttagatcaca tctgtagtgg tctgcatgct   300
attccccgga aaataaagc aagatcggcc aagaaaagat cccacaagtc agctctagga   360
aattctacaa atattcagt ga                                             382

<210> SEQ ID NO 36
<211> LENGTH: 132
<212> TYPE: PRT
<213> ORGANISM: Aegilops tauschii

<400> SEQUENCE: 36

Met Trp Ser Ser Ser Lys Gln Gln Gly Gly Asp Arg Glu Glu Trp Lys
1               5                   10                  15

Gln His Lys Met Val Lys Glu Val Lys Lys Ser Glu Thr Pro Ile Phe
```

```
            20                  25                  30
Thr Tyr Gln Leu Pro Phe His Ser Leu Pro Leu Asn Lys Val Lys Asn
        35                  40                  45
Ile Glu Val Asp Arg Leu Arg Leu Ser Phe Thr Thr Pro Lys Asn Ser
 50                  55                  60
Thr Leu Val Pro Val Asp Ser Gly Ser Asp Glu Glu Ser Asp Glu Asp
 65                  70                  75                  80
Gln Gly Cys Ser Asp Ile Asp Ser Asp Lys Pro Met Asp Glu Val Leu
                85                  90                  95
Asp His Ile Cys Cys Gly Leu His Ala Ile Pro Arg Lys Asn Lys Ala
            100                 105                 110
Arg Ser Ala Lys Lys Arg Ser His Lys Leu Ser Ser Arg Lys Phe Tyr
        115                 120                 125
Lys Ile Phe Ser
        130

<210> SEQ ID NO 37
<211> LENGTH: 133
<212> TYPE: PRT
<213> ORGANISM: Triticum aestivum

<400> SEQUENCE: 37

Met Met Trp Ser Ser Ser Lys Gln Gln Gly Gly Asp Arg Glu Glu Trp
 1               5                   10                  15
Lys Gln His Lys Met Val Lys Glu Val Lys Ser Glu Thr Pro Ile
            20                  25                  30
Phe Thr Tyr Gln Leu Pro Phe His Ser Leu Pro Leu Asn Lys Val Lys
        35                  40                  45
Asn Ile Glu Val Asp Arg Leu Arg Leu Ser Phe Thr Thr Pro Lys Asn
 50                  55                  60
Ser Thr Leu Val Pro Val Asp Ser Gly Ser Asp Glu Glu Ser Asp Glu
 65                  70                  75                  80
Asp Gln Gly Cys Ser Asp Ile Asp Ser Asp Lys Pro Met Asp Glu Val
                85                  90                  95
Leu Asp His Ile Cys Cys Gly Leu His Ala Ile Pro Arg Lys Asn Lys
            100                 105                 110
Ala Arg Ser Ala Lys Lys Arg Ser His Lys Leu Ser Ser Arg Lys Phe
        115                 120                 125
Tyr Lys Ile Phe Ser
        130

<210> SEQ ID NO 38
<211> LENGTH: 130
<212> TYPE: PRT
<213> ORGANISM: Triticum aestivum

<400> SEQUENCE: 38

Met Val Trp Ser Thr Ser Lys Gln Gln Gly Gly Glu Arg Glu Glu Ser
 1               5                   10                  15
Lys Gln His Lys Met Val Lys Glu Val Lys Thr Pro Ile Phe Thr His
            20                  25                  30
Gln Leu Ser Phe His Ser Leu Pro Leu Asn Lys Val Lys Asn Ile Glu
        35                  40                  45
Val Asp Arg Leu Arg Leu Ser Phe Thr Thr Pro Lys Asn Ser Thr Leu
 50                  55                  60
Val Pro Val Asp Ser Gly Ser Asp Glu Glu Ser Asp Glu Asp Arg Gly
```

```
            65                  70                  75                  80

Cys Ser Asp Ile Asp Ser Asn Lys Pro Met Asp Glu Gly Leu Asp His
                85                  90                  95

Ile Cys Ser Gly Leu His Ala Ile Pro Arg Lys Asn Lys Ala Arg Ser
            100                 105                 110

Ala Lys Lys Arg Ser His Lys Ile Ser Ser Arg Lys Phe Tyr Lys Ile
            115                 120                 125

Phe Ser
    130

<210> SEQ ID NO 39
<211> LENGTH: 142
<212> TYPE: PRT
<213> ORGANISM: Hordeum vulgare

<400> SEQUENCE: 39

Met Met Val Trp Ser Thr Ser Lys Gln Gln Gly Gly Asp Arg Ala Glu
1               5                   10                  15

Ser Lys Gln His Lys Met Val Lys Glu Met Lys Ser Ser Glu Thr Pro
                20                  25                  30

Thr Phe Thr Tyr Gln Leu Pro Phe His Ser Leu Ser Leu Asn Lys Val
            35                  40                  45

Lys Asn Ile Glu Val Asp Arg Leu Arg Leu Ser Phe Thr Thr Pro Lys
        50                  55                  60

His Ser Thr Leu Val Pro Val Asp Ser Asp Ser Asp Glu Glu Ser Asp
65                  70                  75                  80

Asp Cys Ser Asp Ile Asp His Ala Val Asn Ser Thr Gly Gly Gln Met
                85                  90                  95

Ala Ala Asp Lys Pro Val Asp Ala Gly Leu Asp His Ile Cys Ser Gly
            100                 105                 110

Leu His Ala Ile Pro Arg Lys Asn Lys Ala Arg Ser Ala Lys Lys Arg
            115                 120                 125

Ser His Lys Leu Ser Ser Arg Lys Phe Tyr Lys Ile Phe Ser
            130                 135                 140

<210> SEQ ID NO 40
<211> LENGTH: 144
<212> TYPE: PRT
<213> ORGANISM: Triticum aestivum

<400> SEQUENCE: 40

Met Val Trp Ser Thr Ser Lys Gln Gln Gly Gly Asp Gln Glu Glu Pro
1               5                   10                  15

Lys Gln His Lys Met Val Lys Glu Val Lys Lys Ser Glu Thr Pro Ile
                20                  25                  30

Phe Thr Tyr Gln Leu Pro Phe His Ser Leu Ser Leu Asn Lys Val Lys
            35                  40                  45

Asn Ile Glu Val Asp Arg Leu Arg Leu Ser Phe Thr Thr Ala Lys Asn
        50                  55                  60

Ser Thr Leu Val Pro Val Asp Ser Gly Ser Glu Glu Ser Asp Glu
65                  70                  75                  80

Asp Gln Gly Cys Ser Asp Ile Asp Asp Thr Val Asn Ser Ile Gly Gly
                85                  90                  95

Gln Met Thr Val Asp Lys Pro Met Asp Glu Gly Leu Asp Arg Ile Cys
            100                 105                 110

Ser Gly Leu His Ala Ile Pro Arg Lys Asn Lys Ala Arg Ser Ala Lys
```

```
            115                 120                 125
Lys Arg Ser His Lys Leu Ser Ser Arg Lys Phe Tyr Lys Ile Phe Ser
    130                 135                 140

<210> SEQ ID NO 41
<211> LENGTH: 121
<212> TYPE: PRT
<213> ORGANISM: Festuca pratensis

<400> SEQUENCE: 41

Met Val Trp Pro Ala Ser Lys Gln Gln Gly Gly Asp Arg Pro Glu
1               5                   10                  15

Ala Lys His His Asn Thr Val Lys Glu Val Lys Ser Gly Thr Pro Ile
                20                  25                  30

Phe Thr Tyr Gln Leu Pro Leu His Ser Leu Ser Leu Asn Lys Val Lys
            35                  40                  45

Asn Ile Glu Val Asp Arg Leu Arg Leu Ser Phe Ala Thr Pro Arg Lys
        50                  55                  60

Pro Ala Leu Val Pro Val Asp Ser Asp Asp Glu Ser His Asp Asp
65                  70                  75                  80

Gln Glu Cys Leu Asp His Ile Cys Ser Ala Ala Met His Ala Val Pro
                85                  90                  95

Arg Lys Asn Lys Ser Arg Ser Thr Lys Lys Arg Val Arg Lys Ala Ser
            100                 105                 110

Tyr Lys Glu Tyr Tyr Lys Ile Phe Ser
        115                 120

<210> SEQ ID NO 42
<211> LENGTH: 131
<212> TYPE: PRT
<213> ORGANISM: Brachypodium distachyon

<400> SEQUENCE: 42

Met Thr Cys Ile Gly Gly Asp His Gly Glu Val Lys Gln Gln Lys
1               5                   10                  15

Val Ala Ala Gln Ser Lys Asn Ala Gly Leu Ile Gln Leu Lys Thr Lys
                20                  25                  30

Lys Ser Glu Asp Pro Met Leu Val His Gln Phe Pro Phe His Asp Leu
            35                  40                  45

Ser Leu Asn Lys Val Lys Asn Ile Glu Val Asp Arg Leu Arg Leu Ser
        50                  55                  60

Pro Val Thr Pro Lys Lys Leu Thr Ser Ala Thr Ala Asp Ser Ala Glu
65                  70                  75                  80

Glu Asn His Glu Asp Gln Asp Pro Glu Thr Leu Lys Thr Asp Glu Arg
                85                  90                  95

Leu Asp Gln Met Cys Ser Phe Leu His Ala Ile Pro Arg Lys Asn Arg
            100                 105                 110

Ser Lys Ser Ser Lys Arg Arg Thr Gln Lys Thr Ser Arg Lys Leu
        115                 120                 125

Cys Arg Phe
    130

<210> SEQ ID NO 43
<211> LENGTH: 119
<212> TYPE: PRT
<213> ORGANISM: Artificial Sequence
<220> FEATURE:
<223> OTHER INFORMATION: CONSENSUS SEQUENCE
```

```
<400> SEQUENCE: 43

Met Val Trp Ser Ser Lys Gln Gln Gly Gly Asp Arg Glu Lys Gln His
1               5                   10                  15

Lys Met Val Lys Glu Val Lys Lys Ser Glu Thr Pro Ile Phe Thr Tyr
                20              25                  30

Gln Leu Pro Phe His Ser Leu Ser Leu Asn Lys Val Lys Asn Ile Glu
            35              40                  45

Val Asp Arg Leu Arg Leu Ser Phe Thr Thr Pro Lys Ser Thr Leu Val
    50              55                  60

Pro Val Asp Ser Ser Asp Glu Glu Ser Asp Asp Gln Cys Ser Asp Ile
65              70                  75                  80

Asp Lys Pro Asp Glu Leu Asp His Ile Cys Ser Gly His Ala Pro Arg
            85                  90                  95

Lys Asn Lys Ala Arg Ser Ala Lys Lys Arg Ser His Lys Ser Ser Arg
            100             105                 110

Lys Phe Tyr Lys Ile Phe Ser
            115
```